(12) United States Patent
Sedivy et al.

(10) Patent No.: US 6,864,224 B1
(45) Date of Patent: Mar. 8, 2005

(54) KINASE INHIBITORS AND METHODS OF USE IN SCREENING ASSAYS AND MODULATION OF CELL PROLIFERATION AND GROWTH

(75) Inventors: John M. Sedivy, Barrington, RI (US); Walter Kolch, Glasgow (GB); Kam Chi Yeung, Barrington, RI (US)

(73) Assignee: Brown University Research Foundation, Providence, RI (US)

( * ) Notice: Subject to any disclaimer, the term of this patent is extended or adjusted under 35 U.S.C. 154(b) by 401 days.

(21) Appl. No.: 09/654,281

(22) Filed: Sep. 1, 2000

Related U.S. Application Data

(60) Provisional application No. 60/151,992, filed on Sep. 1, 1999.

(51) Int. Cl.⁷ .............................................. A61K 38/00
(52) U.S. Cl. .......................................... 512/2; 435/375
(58) Field of Search ..................... 514/2, 363; 435/375

(56) References Cited

U.S. PATENT DOCUMENTS 4,925,677 A * 5/1990 Feijen .......................... 424/423
6,187,799 B1 * 2/2001 Wood et al. ................. 514/363

OTHER PUBLICATIONS

Jelinek et al (Mar. 1996, Molecular and Cellular Biology, vol. 16, pp. 1027–1034).*
Berg et al (Mar. 5, 1999, Cancer Research 59, 1180–1183).*
Kastin, AJ, 2001, Life Science, 69(11): 1305–12.*
Frost, SJ, 1993, J Cell Biochem, 52(2): 227–36.*
Selbo et al (2002, Tumour Biol 23, 103–12, abstract only).*
Yeung et al (May 2000, Molecular and Cellular Biology, vol. 21, pp. 7207–7217).*
Yeung et al (1999, Nature, vol. 401, pp. 173–177).*
Ferrell, Jr., MAP Kinases in Mitogenesis and Development, 1996, *Current Topics in Developmental Biology*, 33: 1–60.
Morrison, et al., The complexity of Raf–1 regulation, 1997, *Cell Biol.*, 9: 174–179.
Moddie, et al., Complexes of Ras–GTP with Raf–1 and Mitogen–Activated Protein Kinase Kinase, 1993, *Science*, 260: 1658–1661.
Schaeffer, et al, MPI: A MEK Binding Partner that Enhances Enzymatic Activation of the MAP Kinase Cascade, 1998, *Science*, 281:1668–1671.

* cited by examiner

*Primary Examiner*—Larry R. Helms
*Assistant Examiner*—Misook Yu
(74) *Attorney, Agent, or Firm*—Palmer & Dodge LLP; Kathleen M. Williams; Elizabeth Spar

(57) ABSTRACT

The invention relates to the discovery of a novel amino acid sequence motif, herein termed the RKIP motif, and to the family of proteins defined by the presence of that motif. Proteins comprising the RKIP motif modulate kinases involved in signal transduction pathways. The RKIP motif forms the basis for screening assays for the identification of agents useful for modulating signal transduction pathways subject to RKIP family mediated regulation, and for the diagnosis and treatment of disorders involving inappropriate activities of pathways subject to RKIP family medicated regulation.

1 Claim, 19 Drawing Sheets

| Bait \ Prey | RKIP (His-prototrophy) | RKIP (β-gal activity) |
|---|---|---|
| BXB | yes | yes |
| Kinase-dead BXB | yes | yes |
| cdk2 kinase | no | no |
| p53 | no | no |
| Lamin | no | no |
Fig. 2a
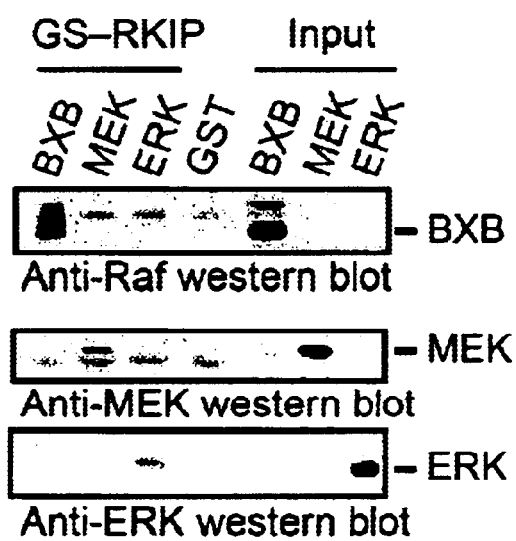
Fig. 2b
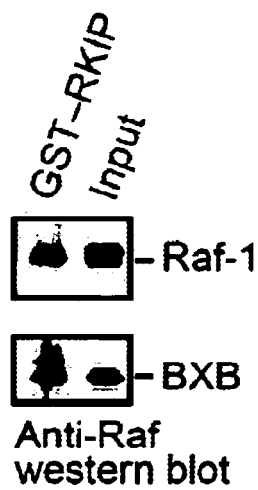
Fig. 2c

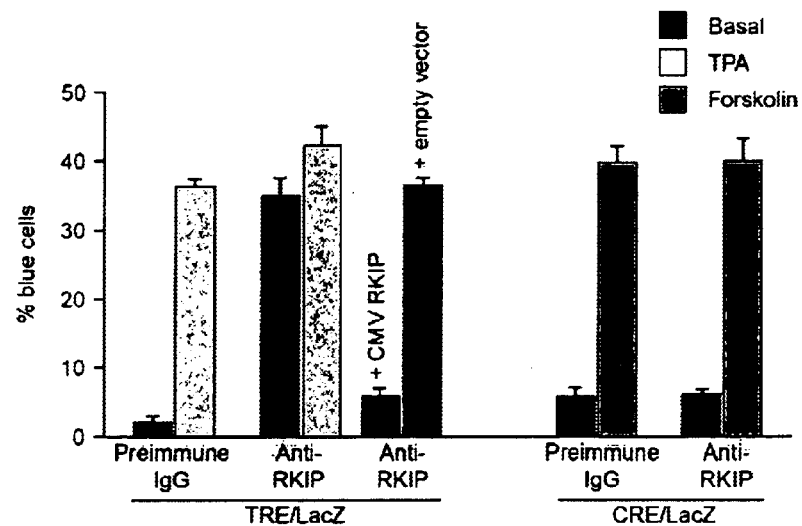
Fig. 3a
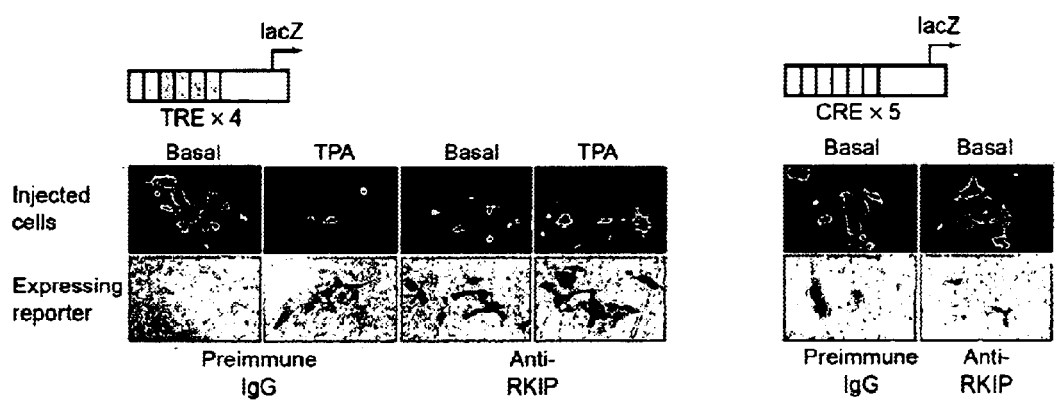
Fig. 3b
Fig. 3c

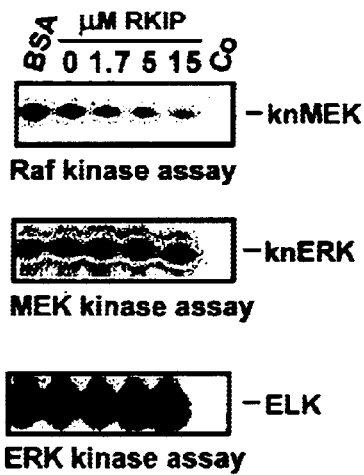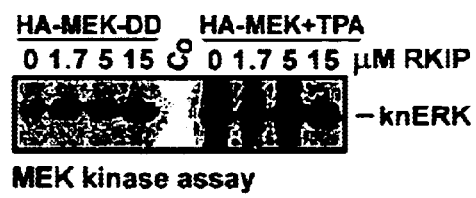
Fig. 5a
Fig. 5b
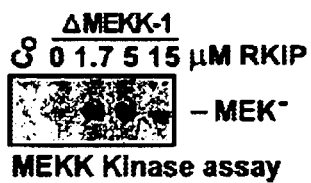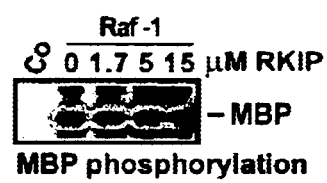
Fig. 5c
Fig. 5d
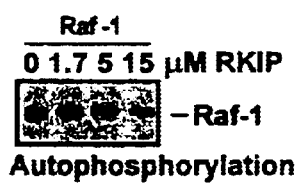
Fig. 5e

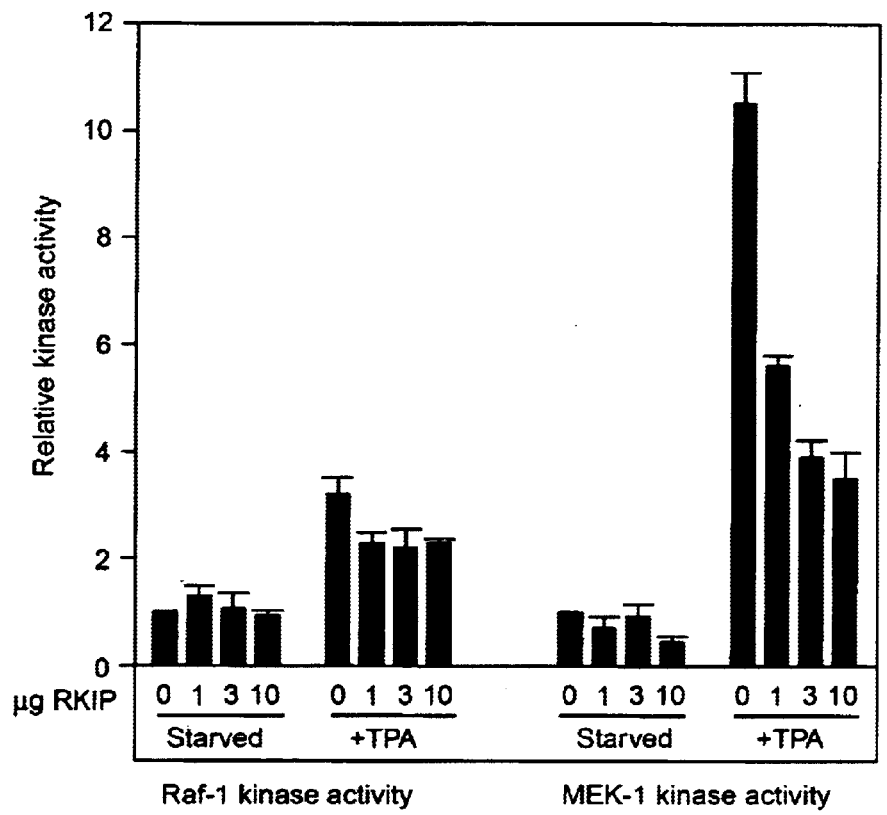
Fig. 6d
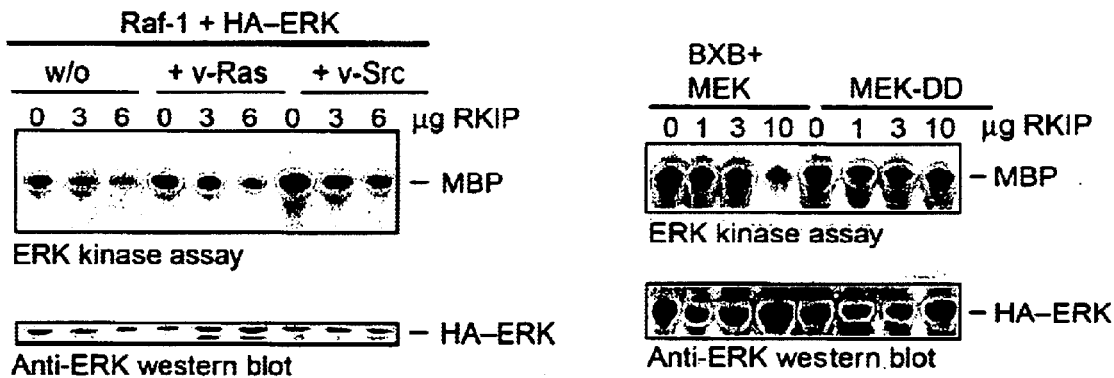
Fig. 6e
Fig. 6f

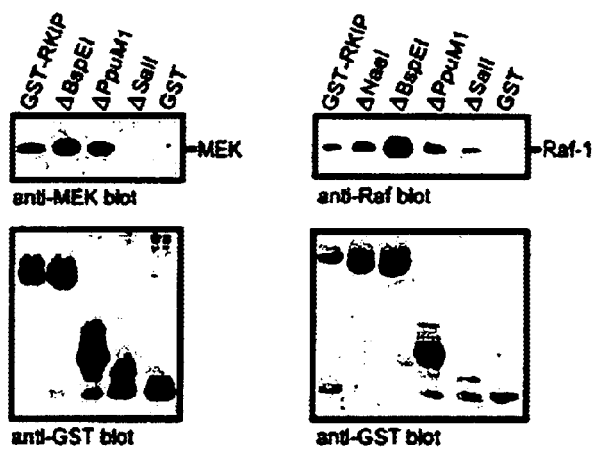
Fig. 11e
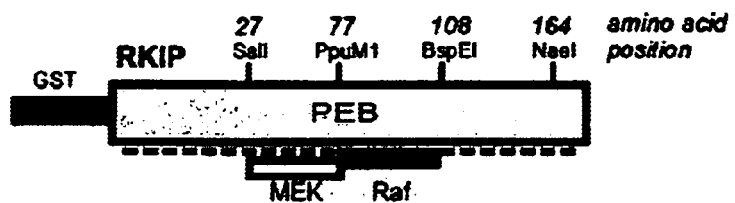
Fig. 11f
Fig. 11g

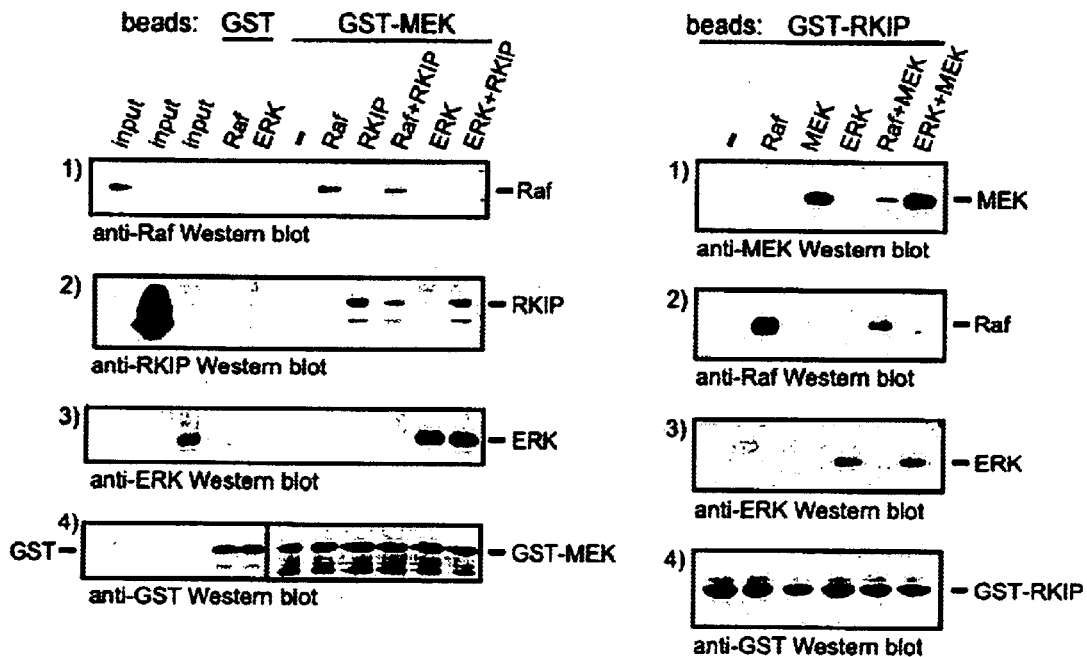
Fig. 12a
Fig. 12b
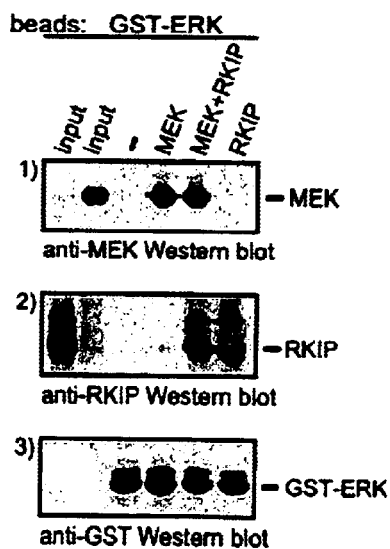
Fig. 12c
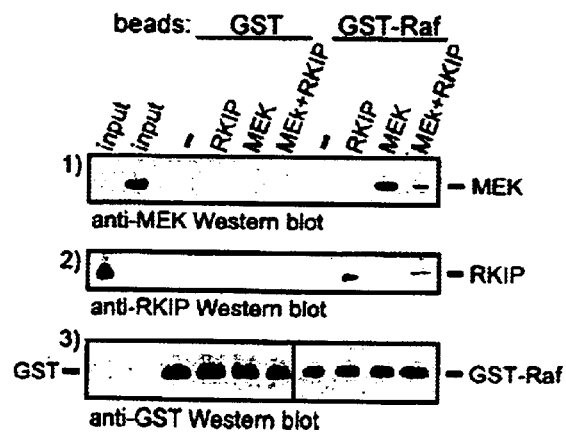
Fig. 12d

KINASE INHIBITORS AND METHODS OF USE IN SCREENING ASSAYS AND MODULATION OF CELL PROLIFERATION AND GROWTH

This application claims the priority of U.S. patent application Ser. No. 60/151,992, filed Sep. 1, 1999.

This application was made using U.S. Government funds, NIH Grant No.: R01GM55435 and therefore, the U.S. Government has rights in the invention.

FIELD OF INVENTION

The present invention relates, in general, to identification of a novel class of protein kinase inhibitors; to therapeutic agents that interact with members of the class of kinase inhibitors; and their use in modulating cell proliferation and growth.

BACKGROUND OF THE INVENTION

Raf-1 phosphorylates and activates MEK-1, a kinase that activates the extracellular signal regulated kinases, ERKs. This kinase cascade governs the proliferation and differentiation of different cell types (Ferrel Jr. Curr. Top. Dev. Biol. 33:1–60, 1996; Morrison and Cutler, Curr. Opin. Cell Biol. 9:174–179, 1997).

In metazoans the Ras/Raf-1/MEK/ERK module is a ubiquitously expressed signaling pathway that conveys mitogenic and differentiation signals from the cell membrane to the nucleus (Ferrel Jr. Curr. Top. Dev. Biol. 33:1–60, 1996). This kinase cascade appears to be spatially organized in a signaling complex nucleated by Ras proteins (Moodie et al. Science 260:1658–1661, 1993). The regulation of the Ras/Raf-1/MEK/ERK module is complex and may include associations with scaffolding and regulatory proteins (Schaeffer et al. Science 281:1668–1671, 1998).

SUMMARY OF THE INVENTION

The present invention relates, in general, to the identification of a novel class of protein kinase inhibitors, to agents that interact with members of the class of kinase inhibitors, and to the use of such agents in modulating signal transduction pathways involving kinases responsive to those inhibitors. The invention also relates to the diagnosis of disorders or diseases related to or associated with inappropriate activity or expression of this class of protein kinase inhibitors. More specifically, the invention relates to a novel family of protein kinase inhibiting molecules that comprise a newly identified evolutionarily conserved motif termed the RKIP motif, for Raf-1 Kinase Inhibitory Protein motif.

The invention encompasses a method of identifying an agent that modulates a signal transduction pathway, the method comprising the steps of: (i) providing a polypeptide comprising an RKIP motif; and (ii) contacting the polypeptide with a candidate agent, wherein binding of the candidate agent to the RKIP motif is indicative that the candidate agent is a signal transduction modulating agent.

In one embodiment, the binding is detected using a method selected from the group consisting of surface plasmon resonance, yeast two-hybrid assay, pull-down assay, FRET, fluorescence polarization assay, scintillation proximity assay, transcription assay, kinase assay and transformation assay.

In another embodiment, the modulation is an increase in the activity of the signal transduction pathway.

In another embodiment, the modulation is a decrease in the activity of the signal transduction pathway.

The invention further encompasses a method of identifying an agent that modulates cell growth, the method comprising the steps of: (i) providing a polypeptide comprising an RKIP motif; and (ii) contacting the polypeptide with a candidate agent, wherein binding of the candidate agent to the RKIP motif is indicative that the candidate agent is a cell growth modulating agent.

In one embodiment, the binding is detected using a method selected from the group consisting of surface plasmon resonance, yeast two-hybrid assay, pull-down assay, FRET, fluorescence polarization assay, scintillation proximity assay, transcription assay, kinase assay and transformation assay.

In another embodiment, the modulation is an increase in cell growth.

In another embodiment, the modulation is a decrease in cell growth. Preferably the agent causes that decrease in cell growth in a tumor.

The invention further encompasses a method of identifying an agent that modulates apoptosis, said method comprising the steps of: (i) providing a polypeptide comprising an RKIP motif; and (ii) contacting the polypeptide with a candidate agent, wherein binding of the candidate agent to the RKIP motif is indicative that the candidate agent is an apoptosis-modulating agent.

In one embodiment, the binding is detected using a method selected from the group consisting of surface plasmon resonance, yeast two-hybrid assay, pull-down assay, FRET, fluorescence polarization assay, scintillation proximity assay, transcription assay, kinase assay and transformation assay.

In another embodiment, the modulation is an increase in apoptosis. Preferably the agent causes that modulation in a tumor.

In another embodiment, the modulation is a decrease in apoptosis.

The invention further encompasses a method of identifying an agent that modulates an RKIP-sensitive pathway, the method comprising the steps of: (i) providing a polypeptide comprising an RKIP motif; and (ii) contacting the polypeptide with a candidate agent, wherein binding of the candidate agent to the RKIP motif is indicative that the candidate agent is a modulator of an RKIP-sensitive pathway.

In one embodiment, the binding is detected using a method selected from the group consisting of surface plasmon resonance, yeast two-hybrid assay, pull-down assay, FRET, fluorescence polarization assay, scintillation proximity assay, transcription assay, kinase assay and transformation assay.

In another embodiment, the modulation is an increase in the activity of an RKIP-sensitive pathway.

In another embodiment, the modulation is a decrease in the activity of an RKIP-sensitive pathway. Preferably the agent decreases the activity in a in a tumor cell.

The invention further encompasses a method of identifying an agent that modulates the activity of an RKIP motif-containing polypeptide, the method comprising the steps of: i) providing an RKIP motif-containing polypeptide and a polypeptide binding partner thereof; and ii) contacting the RKIP motif-containing polypeptide and the binding partner thereof under conditions permitting the binding of the RKIP motif-containing polypeptide to the binding partner thereof; and iii) monitoring the association of the RKIP motif-containing polypeptide and the binding partner thereof in the presence and absence of a candidate agent, wherein an increase or decrease in the binding of the RKIP motif-containing polypeptide to the binding partner thereof is indicative that the candidate agent modulates the activity of an RKIP motif containing polypeptide.

In one embodiment, the monitoring is performed using a method selected from the group consisting of: surface plasmon resonance, yeast two-hybrid assay, pull-down assay, FRET, fluorescence polarization assay and scintillation proximity assay.

The invention further encompasses a method of identifying an agent that modulates the activity of an RKIP motif-containing polypeptide, the method comprising the steps of: i) providing a cell comprising a reporter gene construct wherein the expression of the reporter gene is functionally coupled to a control region regulated by an RKIP-sensitive kinase; and ii) measuring the amount of reporter gene expression from the construct in the presence and absence of a candidate agent, wherein an increase or decrease in the expression of the reporter is indicative that the candidate agent modulates the activity of an RKIP motif-containing polypeptide.

In one embodiment, the expression of the reporter gene is controlled by an AP-1 sensitive control region which is functionally coupled to the reporter gene.

In another embodiment, the expression of the reporter gene is controlled by an NF-κB sensitive control region which is functionally coupled to the reporter gene.

The invention further encompasses a method of detecting a condition associated with the activity of an RKIP-sensitive signal transduction pathway comprising: a) measuring the amount of an RKIP motif-encoding RNA present in a tissue sample; and b) comparing the amount of an RKIP motif-encoding RNA present in the sample to the amount of the RKIP motif-encoding RNA present in a control tissue sample present in a control tissue sample, wherein an increase or decrease in the amount of the RKIP motif-encoding RNA relative to the amount of the RKIP motif-encoding RNA in the control tissue sample is indicative of a condition associated with the activity of an RKIP-sensitive signal transduction pathway.

In one embodiment, the measuring is performed by a method selected from the group consisting of RT-PCR, RNase protection, in situ hybridization and Northern hybridization.

The invention further encompasses a method of detecting a condition associated with the activity of an RKIP-sensitive signal transduction pathway comprising: a) measuring the amount of an RKIP motif-containing polypeptide present in a tissue sample; and b) comparing the amount of an RKIP motif-containing polypeptide present in the sample to the amount of an RKIP motif-containing polypeptide present in a control tissue sample, wherein an increase or decrease in the amount of the RKIP motif-containing polypeptide relative to the amount of the RKIP motif-containing polypeptide in the control tissue sample is indicative of a condition associated with the activity of an RKIP-sensitive signal transduction pathway.

In one embodiment, the condition is cancer.

In another embodiment, the measuring is performed by measuring the binding of an antibody to said RKIP motif-containing polypeptide or an antigen-binding fragment thereof.

The invention further encompasses a method of identifying an agent that modulates the RKIP-sensitive phosphorylation of a polypeptide, comprising the steps of: a) providing a system that permits phosphorylation of the polypeptide by an RKIP-sensitive kinase; and b) detecting phosphorylation of the polypeptide in the presence and absence of a candidate agent wherein an increase or decrease in phosphorylation is indicative that the agent is a modulator of the RKIP-sensitive phosphorylation of the polypeptide.

In one embodiment, the RKIP-sensitive kinase is selected from the group consisting of Raf, MEK, ERK, NIK and TAK. Preferably the RKIP-sensitive kinase is a human RKIP-sensitive kinase.

The invention further encompasses a method of inhibiting the activity of an RKIP-sensitive kinase, comprising the step of contacting said RKIP-sensitive kinase with an amount of an agent which inhibits the activity of the RKIP-sensitive kinase sufficient to inhibit the activity. An amount sufficient to inhibit the activity is that amount necessary to cause a decrease in the activity of an RKIP-sensitive kinase as defined herein.

In one embodiment, the agent is a polypeptide.

In another embodiment, the polypeptide comprises an RKIP motif.

In another embodiment, the kinase is a MPAK/ERK kinase.

In another embodiment, the agent binds to Raf-1.

The invention further encompasses a method of treating a disorder that is associated with inappropriate expression or activity of an RKIP family polypeptide comprising administering an effective amount of a pharmaceutical composition comprising an agent that modulates the activity of an RKIP family polypeptide to an individual in need of treatment for a cell proliferative disorder.

The invention further encompasses a method of treating a disorder that is associated with inappropriate activity of an RKIP-sensitive signal transduction pathway comprising administering an effective amount of a pharmaceutical composition comprising an agent that modulates the activity of an RKIP family polypeptide to an individual in need of treatment for a disorder that is associated with inappropriate activity of an RKIP-sensitive signal transduction pathway.

The invention further encompasses a polypeptide consisting essentially of an RKIP motif.

The invention further encompasses an RKIP motif fusion protein.

The invention further encompasses an RKIP motif-containing fusion protein.

The invention further encompasses an isolated nucleic acid encoding an RKIP motif cassette.

In one embodiment, the nucleic acid encoding an RKIP motif cassette comprises a vector sequence.

In another embodiment, the nucleic acid encoding an RKIP motif cassette is linked to sequences encoding a heterologous amino acid sequence such that the vector encodes a fusion protein comprising an RKIP motif.

Definitions

The term "RKIP motif" means a motif on a polypeptide characterized by the consensus amino acid sequence TLX$_3$DPD(Z)PX$_3$(B)X4EX$_2$H X$_n$YX$_4$PX$_{(2-4)}$GXHR(O)VX(Z)X$_3$Q (SEQ ID NO:1) wherein the single letter amino acid code is in accordance with the IUB/IUPAC code, X may be any amino acid, Z indicates a hydrophobic amino acid residue, B indicates negatively charged amino acid residue (D or E), O indicates an aromatic amino acid residue (Y or F), and n is an integer from about 10 to about 50. A sequence does not have to be a perfect match with the consensus in order to be an RKIP motif, but must be comprised within a β fold structure composed of two antiparallel β sheets within the molecule. A sequence that is an RKIP motif is at preferably at least about 70% similar to the consensus sequence, more preferably about 75% similar, 80% similar, 85% similar, 90% similar, 95% similar, 98% similar or even 100% similar or most preferably, identical to the consensus. Further, the RKIP sequence motif and polypeptides comprising it interact specifically with one or more signal transduction kinases.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443–453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915–10919). Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

The term "RKIP motif cassette" refers to a nucleic acid sequence consisting essentially of sequence encoding a polypeptide that is an RKIP motif as defined herein.

As used herein, the term "heterologous amino acid sequence" refers to an amino acid sequence that is not comprised by or drawn from an RKIP family member.

As used herein, the term "fusion protein" refers to a polypeptide comprising linked regions or domains from two or more polypeptides that are not expressed in a linked manner in nature. An "RKIP motif fusion protein" is the sequence encoded by an RKIP motif cassette linked to a heterologous protein domain or domains. An "RKIP motif-containing fusion protein", in contrast, may include more of the RKIP family protein than the RKIP motif alone, up to and including the entire RKIP family member protein.

As used herein, the term "signal transduction pathway" refers to a system within a cell that transmits information from outside the cell to the cell nucleus, resulting in a change in the expression of one or more genes. Signal transduction pathways most frequently involve the interactions of protein factors that regulate enzymatic activities (e.g., phosphorylation, protease activity) or the association of signal transducing factors with other factors in a cascade of interactions, wherein the cascade serves to amplify and/or direct a signal to a particular set of genes. The term "activity of a signal transduction pathway" refers to both the effect of the signal transduction pathway on the expression of a gene or genes in response to a signal originating outside the cell and to the individual activities (e.g., association or enzyme activity) of the factors that participate in the pathway. Methods of measuring signal transduction pathway activity are described herein or known in the art. The activity of a signal transduction pathway is herein considered increased if it is increased by at least 10%, and preferably at least 20%, 35%, 50%, 75%, 100%, or even 2-fold, 5-fold, 10-fold, 50-fold or more relative to a standard (e.g., normal tissue or cells or tissue or cells not treated with an agent that modulates that pathway). The activity of an RKIP motif-containing polypeptide is considered decreased if an effector function of such polypeptide, as measured by any of the assay methods described herein, is reduced by at least 10%, and preferably at least 20%, 35%, 50%, 75%, 90%, 95%, or even up to and including 100% (i.e., no activity) relative to a standard.

The term "signal transduction kinase" refers to a kinase that is involved in one or more pathways involved in the transmission of signals originating outside the cell to the nucleus. Examples of signal transduction kinases include, but are not limited to Src, Raf- 1 (GenBank Accession No. NM_002880), MEK, MEKK, MEKKK, ERK-1, ERK-2, NIK (GenBank Accession No. Y10256), TAK (GenBank Accession No. D76446), etc. of a cell for example, a kinase of the Raf/MEK/ERK or NF-κB signal transduction pathways. The "activity" of a signal transduction kinase is defined as the phosphorylation of target proteins. Alternatively, or in addition, "activity" of signal transduction proteins or the signal transduction pathway refers to the biological result of the phosphorylating activity of the kinase, including, for example, cell proliferation, apoptosis, and cell transformation. The activity of a signal transduction pathway may be measured using methods known in the art or described herein, including, for example kinase assays, binding assays (surface plasmon resonance, yeast two-hybrid, FRET, etc.), transcription assays and/or transformation assays. Signal transduction activity is modulated (increased or decreased) if a measurable parameter of signal transduction activity, including, but not limited to, kinase activity, transcription and/or translation of one or more genes or reporter constructs responsive to that signal transduction pathway, or transformation is increased or decreased by at least 10%, and preferably by 20%, 35%, 50%, 75%, 90%, 95% or more, up to and including 100%, and, in the case of an increase, up to 5-fold, 10-fold, 20 fold, or even 50-fold or more.

The term "RKIP family" means polypeptides or proteins that comprise an RKIP motif as defined herein. In addition to an RKIP motif, all proteins belonging to the RKIP family have 1) a characteristic β fold structure formed by two anti-parallel β sheets, 2) a cavity capable of accepting an anion (preferably a phosphoryl moiety), and 3) the ability to specifically interact (or bind) with one or more signal transduction kinases. A protein belonging to the RKIP family preferably includes the RKIP motif with the functional conserved amino acid residues indicated by arrows in FIG. 1.

"RKIP responsive reporter" or "reporter gene construct" refers to a nucleic acid construct comprising a sequence encoding a detectable marker activity that is operatively linked to expression control region(s) that is (are) regulated by a signal transduction pathway that is influenced by an RKIP motif-bearing polypeptide. Examples of reporter activities include, but are not limited to luciferase, GFP, CAT, β-gal, secreted alkaline phosphatase, and human growth hormone. Examples of RKIP-responsive sequence elements are those involved in AP-1 transactivation and NF-κB transactivation.

As used herein, the term "functionally coupled", used in reference to a reporter gene construct and a control region means that changes leading to an increase or decrease in the activity of the control region cause a proportional increase or decrease in the expression of the reporter gene.

As used herein, the term "AP-1 sensitive control region" refers to a nucleic acid sequence element which binds an AP-1 transcription factor activity and mediates the transactivation of a reporter gene in response to that binding. The consensus AP-1 binding site is taught herein and known in the art. The AP-1 sensitive control region may be drawn from a specific gene (i.e., a naturally-occurring AP-1 binding element) or it may be a consensus AP-1 element, a set of repeated consensus elements, or a set of repeated naturally-occurring AP-1 binding elements.

As used herein, the term "NF-κB sensitive control region" refers to a nucleic acid sequence element which binds an NF-κB transcription factor activity and mediates the transactivation of a reporter gene in response to that binding. The consensus NF-κB binding site is taught herein and known in the art. The NF-κB sensitive control region may be drawn from a specific gene (i.e., a naturally-occurring NF-κB binding element) or it may be a consensus NF-κB element, a set of repeated consensus elements, or a set of repeated naturally-occurring NF-κB binding elements.

As used herein, the term "RKIP-sensitive" refers to the property of a protein or a pathway comprising that protein wherein increases or decreases in the expression or activity of an RKIP-motif-containing polypeptide result in a modulation of the activity of that protein or the pathway in which that protein is active. As used herein, the term "RKIP-sensitive phosphorylation" refers to phosphorylation of a polypeptide that is positively or negatively influenced by changes in the expression or activity of one or more RKIP motif-containing polypeptides.

As used herein, the term "condition associated with the activity of an RKIP-sensitive signal transduction pathway" refers to a disease or disorder characterized by the inappropriate activity of a signal transduction pathway that is sensitive to an RKIP motif-containing polypeptide. One may determine whether a pathway is RKIP-sensitive by either overexpressing an RKIP motif-containing polypeptide in cells in which that pathway is active, or by exposing such cells to an agent that modifies and/or mimics the activity of an RKIP motif-containing polypeptide and measuring the activity of the pathway as described herein. An increase or decrease in the activity of the pathway under such conditions is indicative that the pathway is RKIP-sensitive. The activity of a signal transduction pathway is "inappropriate" if the expression of one or more genes regulated by that pathway is increased or decreased in a disease or disorder relative to the expression of such a gene or genes in a normal individual.

As used herein, a "cell proliferative disease" is a disease or disorder characterized by the inappropriate growth or multiplication of one or more cell types relative to the growth of that cell type or types in an individual not suffering from that disease.

The term "antigen binding fragment thereof" when used in relation to an antibody refers to fragments of an antibody which are also specifically reactive with a vertebrate, e.g., mammalian, protein. Antibodies can be fragmented using conventional techniques and the fragments screened for utility in the same manner as whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies as used herein includes polyclonal, monoclonal, or other purified preparations of antibodies and recombinant, including, but not limited to, humanized antibodies.

The term "transcriptional regulatory sequence" is a generic term used to refer to DNA sequences, such as initiation signals, enhancers, and promoters, which induce or control transcription of protein coding sequences to which they are operatively linked. In preferred embodiments, transcription of one of the genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally occurring forms of the polypeptide.

The term "agent" means a composition that has the capacity to modify the bioactivity of a nucleic acid encoding or polypeptide comprising an RKIP motif so as to modulate the activity of a signal transduction pathway that is responsive to an RKIP family protein. An "agent" as used herein may either promote or inhibit the function of the signal transduction pathway, the expression of genes regulated by that pathway, or the ultimate outcome of that pathway's activation (e.g., proliferation, apoptosis, differentiation, etc.). Agents can include any recombinant, modified or natural nucleic acid molecule, library of recombinant, modified or natural nucleic acid molecules, synthetic, modified or natural peptide, library of synthetic, modified or natural peptides; organic or inorganic compound, or library of organic or inorganic compounds (including small molecules) where the agent has the capacity to modify the bioactivity of an RKIP motif-bearing polypeptide.

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

"Bioactivity" or "activity", which are used interchangeably, herein mean an effector or antigenic function that is directly or indirectly performed by a polypeptide (whether in its native or denatured conformation), or by any subsequence thereof. Bioactivities include binding to polypeptides, binding to other proteins or molecules, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene. The activity of an RKIP motif-containing polypeptide is increased by a modulating agent if an effector function of such polypeptide, as measured by any of the assay methods described herein (e.g., partner binding assays, transcription assays, transformation assays, kinase assays, etc.), is increased by at least 10%, and preferably at least 20%, 35%, 50%, 75%, 100%, or even. 2-fold, 5-fold, 10-fold, 50-fold or more relative to a sample in which no agent was present. The activity of an RKIP motif-containing polypeptide is decreased by a modulating agent if an effector function of such polypeptide, as measured by any of the assay methods described herein, is reduced by at least 10%, and preferably at least 20%, 35%, 50%, 75%, 90%, 95%, or even up to and including 100% (i.e., no activity).

The term "increase" as used herein refers to a function of an "agonist" which is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

As used herein, the term "conditions permitting the binding of an RKIP motif-containing polypeptide to a binding partner" refers to those conditions of, for example, salt concentration, pH, temperature, oxidation/reduction potential, protein concentration, etc. under which a given partner binds to an RKIP motif-containing polypeptide. Generally, protein:protein interactions will occur under physiological conditions of salt, temperature, pH and redox potential.

As used herein, the term "polypeptide binding partner" refers to a polypeptide that specifically binds to an RKIP motif-containing polypeptide.

As used herein, the term "monitor the association" refers to measurement of the interaction of an RKIP motif-containing polypeptide with a binding partner (e.g., a polypeptide or other molecule). Such measurement is accomplished by methods as taught herein or as known in the art.

The term "cell" as used herein means the smallest structural unit of an eukaryotic organism that is capable of independent functioning, comprising one or more nuclei, cytoplasm, and various organelles that are surrounded by a semi-permeable plasma membrane.

The term "growth" of a cell refers to the proliferative state of a cell as well as to its differentiative state. Accordingly, the term refers to the phase of the cell cycle in which the cell is, e.g., $G_0$, or actively cycling ($G_1$, S, $G_2$, M), as well as to its state of differentiation, e.g., undifferentiated, partially differentiated, or fully differentiated. Without wishing to be limited, differentiation of a cell is usually accompanied by a decrease in the proliferative rate of a cell.

The term "inhibit" refers to a function by an "antagonist" which refers to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present. An antagonist bioactivity if it reduces that activity by at least 10%, preferably by at least 20%, 30%, 50%, 75%, 95%, 98%, and up to and including 100%.

Inhibition of expression can be monitored using mRNA quantification methods known in the art. Such methods include but are not limited to Northern blot hybridization, RNase protection, and RT-PCR.

The term "interact" as used herein is meant to include detectable interactions (e.g., biochemical interactions) between molecules, such as protein-protein, protein-nucleic acid, nucleic acid-nucleic acid, and protein-organic or inorganic molecule or nucleic acid- organic or inorganic molecule interactions. A molecular interaction is "specific" if a molecule interacts with one or more target partners while excluding non-target molecules within a given sample.

The term "recombinant protein" refers to a polypeptide produced by recombinant DNA techniques, wherein generally, DNA encoding a polypeptide is inserted into a suitable expression vector which is in turn used to transform a host cell to produce the encoded protein. Moreover, the phrase "derived from", with respect to a recombinant gene, is meant to include within the meaning of "recombinant protein" those proteins having an amino acid sequence of a native polypeptide, or an amino acid sequence generated by mutations including substitutions and deletions (including truncation) and/or additions to a the polypeptide sequence as it occurs in nature.

"Binding" as used herein means physical interaction between two molecules. The term refers to binding that is "specific", in that the a binding molecule interacts with one or more target partners while excluding non-target molecules within a given sample. It is preferred, although not absolutely necessary, that binding result directly or indirectly in a change in a measurable characteristic of a sample. As used herein, binding is "inhibited" when a measure of the amount of a molecule bound decreases by at least 10%, and preferably by at least 20%, 50%, 75%, 80% 90%, 98% or more, up to and including 100% (no binding) relative to a chosen standard (e.g., a sample that does not contain a known or suspected inhibitor). Conversely, binding is "increased" or "enhanced" when a measure of the amount of a molecule bound increases by at least 10%, and preferably by at least 20%, 50%, 75%, 80% 90%, 98% or more, up to and including 100% or even more, including 2-fold, 5-fold, 10-fold or more relative to a chosen standard. Binding may be measured in a number of ways known to those of skill in the art, including but not limited to surface plasmon resonance, fluorescence polarization, FRET, scintillation proximity, pull-down assays, and yeast two-hybrid assays.

As used herein, "stringent conditions" means hybridization will occur only if there is at least 95%, preferably at least 97%, and optimally 100% identity or complementarity between the probe and the sequences it binds. Specific solution compositions and methods for hybridization under stringent conditions are described herein below.

For membrane hybridization (e.g., Northern hybridization), stringent conditions are defined as incubation with a radiolabeled probe in 5×SSC, 5× Denhardt's solution, 1% SDS at 65° C. Stringent washes for membrane hybridization are performed as follows: the membrane is washed at room temperature in 2×SSC/0.1% SDS and at 65° C. in 0.2×SSC/0.1% SDS, 10 minutes per wash, and exposed to film.

For in situ hybridization using RNA probes ("riboprobes" transcribed in vitro from a DNA template according to methods known in the art), stringent conditions are defined as: Radiolabeled probe (e.g., 35S-labeled riboprobe), mixed with an amount of non-specific competitor RNA (generally transcribed from a vector without a probe template insert) approximately equal to one half the mass of labeled probe is heated at 100° C. for 3 minutes, followed by addition of hybridization buffer (50% (v/v) deionized formamide, 0.3 M NaCl, 10 mM Tris (pH 8.0), 1 mM EDTA, 1× Denhardt's solution, 500 mg/ml yeast tRNA, 500 mg/ml poly(A), 50 mM DTT, 10% polyethylene glycol 6000), to 0.3 µg/ml final probe concentration (estimate of amount of probe synthesized is based on calculation of the percent of the label incorporated and the proportion of the labeling base in the probe molecule as a whole). The probe/hybridization mix is incubated at 45° C. until applied to sample slides as a thin layer of liquid. Hybridization reactions are then incubated in a moist chamber (closed container containing towels moistened with 50% deionized formamide, 0.3 M NaCl, 10 mM Tris (pH 8.0), 1 mM EDTA) at 45° C. If background proves to be a problem, a 1 to 2 hour pre-hybridization step using only non-specific, unlabeled riboprobe competitor in hybridization buffer can be added prior to the step in which labeled probe is applied.

Stringent hybridization is carried out for 30 minutes to 4 hours, followed by washing to remove the unbound probe. Samples are washed in an excess (100 ml each wash) of the following buffers: 50% formamide, 2×SSC, 20 mM β-mercaptoethanol, two times, for 15 minutes at 55° C.; 50% formamide, 2×SSC, 20 mM β-mercaptoethanol, 0.5% Triton X-100, two times, for 15 minutes at 55° C.; and 2×SSC, 20 mM. β-mercaptoethanol, two times, for 2 minutes at 50° C. The samples are then subjected to an RNase digestion for 15 minutes at room temperature using a solution containing 40 $\mu$g/ml RNase A, 2 $\mu$g/ml RNase T1, 10 mM Tris (pH 7.5), 5 mM EDTA and 0.3 M NaCl. After RNase digestion, slides are soaked two times for 30 minutes each in 2×SSC, 20 mM β-mercaptoethanol at 50° C., followed by two washes in 50% formamide, 2×SSC, 20 mM β-mercaptoethanol at 50° C. and two washes of 5 minutes each in 2×SSC at room temperature. Hybridized, washed slides are dehydrated through successive two minute incubations in the following: 50% ethanol, 0.3 M ammonium acetate; 70% ethanol, 0.3 M ammonium acetate; 95% ethanol, 0.3 M ammonium acetate; 100% ethanol. Slides are air dried overnight, followed by coating with emulsion for autoradiography according to standard methods.

The term "tissue sample" as used herein means fresh, frozen, or embedded cells, cultured cells, as well as blood and solid tissue samples from a mammal, typically a human. A "control tissue sample" or "standard tissue sample" is a sample taken from either an individual not suffering from a disease or disorder or from an unaffected area of an individual suffering from a disorder. The control or standard is used for comparison with a tissue sample that is being evaluated for a disease or disorder or for the inappropriate expression or activity of an RKIP-sensitive signal transduction pathway.

The term "RKIP identifying agent" means any molecule which specifically binds either an RKIP family member or the nucleic acid encoding an RKIP family member including but not limited to synthetic or isolated nucleic acids; recombinant and isolated proteins and peptides including antibodies; and organic or inorganic molecules. For example, an antibody can recognize all or a part of an RKIP family member. The term "antibody" as used herein is intended to include whole antibodies of any isotype (IgG, IgA, IgM, IgE, etc), and fragments thereof which are also specifically reactive with a vertebrate, e.g., mammalian, protein. Antibodies can be fragmented using conventional techniques and the fragments screened for utility in the same manner as whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites.

As used herein, the term "effective amount" used in relation to a pharmaceutical preparation refers to the amount required to ameliorate the symptoms of the disease or disorder being treated, generally by at least about 10%, and preferably more. An effective amount will vary with the nature of the disease or disorder and with the nature of the agent, but the amount may be determined, and/or adjusted by the administering physician.

BRIEF DESCRIPTION OF FIGURES

FIG. 5 shows that RKIP specifically blocks MEK phosphorylation by Raf-1. a) Effect of RKIP on the activation steps of the Raf/MEK/ERK cascade reconstituted in vitro with purified recombinant proteins. "BSA" 15 $\mu$M bovine serum albumin; "Co." substrate alone; "kn", kinase negative mutant. b) RKIP does not inhibit activated MEK. HA-MEK-DD or HA-MEK-1 expressed in COS-1 cells were immunoprecipated with anti-HA antibodies from serum starved cells or TPA treated cells, respectively, and assayed for kinase activity. c) RKIP does not inhibit MEK phosphorylation by MEKK-1. ΔMEKK-1 was immunoprecipitated from transiently transfected COS-1 cells and used to phosphorylate knMEK. d) RKIP does not inhibit Raf-1 autophosphorylation or phosphorylation of myelin basic protein (MBP).

FIG. 12 shows an analysis of the composition of RKIP protein complexes. (a) GST-MEK beads were incubated with RKIP, Raf, and MEK in the indicated combinations. GST-RKIP beads (b), GST-ERK beads (c), or GST-Raf-1 beads (d) were incubated with recombinant purified proteins as indicated. Incubations were done as described in Materials and Methods, and associated proteins were visualized by Western blotting.

DETAILED DESCRIPTION

Figure 1:
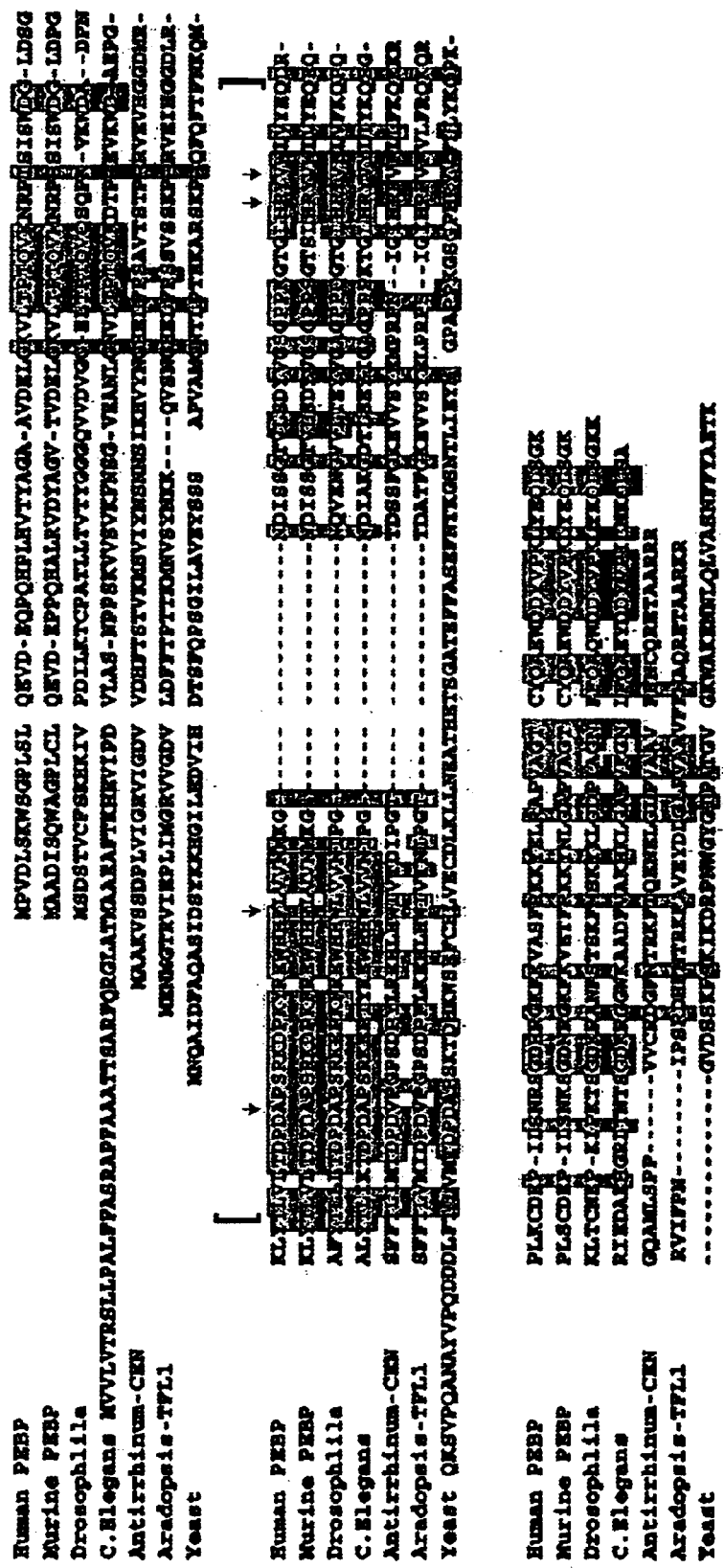
FIG. 1 shows a sequence alignment of amino acid sequences of several RKIP family member proteins. The brackets above the alignment depict the RKIP motif, and the arrows indicate residues shown to be necessary for RKIP activity (Human PEBP (SEQ ID NO:2); Murine PEBP (SEQ ID NO:3); Drosophila (SEQ ID NO:4); C. Elegans (SEQ ID NO:5); Antirrhinum-CEN (SEQ ID NO:6); Aradopsis-TFL1 (SEQ ID NO:7); Yeast (SEQ ID NO:8)).

The present invention relates to identification of a novel class of protein kinase inhibitors, methods of screening candidate agents for modulation of cell growth, and the use of such agents as pharmaceuticals. More particularly, the invention provides methods by which agents can be screened for their ability to affect gene expression or protein interactions involving a newly identified inhibitory motif, the Raf-1 kinase inhibitor protein (RKIP) motif, that is carried by a family of proteins involved in the regulation of intracellular signal transduction pathways. Methods are provided for screening candidate agents for modulation (inhibition or activation) of such signal transduction pathways by specifically affecting members of the family of proteins comprising the RKIP motif or nucleic acids encoding RKIP motif.

The following detailed description discloses how to obtain or make the RKIP motif of the invention, how to use proteins bearing the RKIP motif to identify factors and agents interacting with the RKIP motif, how to identify agents that modify interactions between an RKIP motif and a binding factor; and methods of using such agents for diagnostic and therapeutic purposes.

A. RKIP and the RKIP Motif

The invention is based in part upon the discovery of a conserved functional amino acid sequence element involved in the regulation of signal transduction kinases.

1. Identification of RKIP.

The RKIP motif of the present invention was identified by its interaction with proteins of the ERK pathway using cDNA libraries in a yeast two-hybrid system. The yeast two-hybrid assay used in the present invention was based on a process used by Li et al. (1995, EMBO J. 14:685–696). The yeast two-hybrid assay is a yeast-based genetic assay designed to detect protein-protein interactions in vitro. A positive result obtained with the two-hybrid assay allows identification of genes, for example, from a cDNA library, that encode proteins that interact in vivo with a target protein. The method is based on the modular nature of many transcriptional regulatory proteins. The DNA binding and transcriptional activation functions of such regulatory proteins are often performed by distinct and separable domains of the proteins, such that the domains and their functions may be transferred as modules between proteins. In the two-hybrid system, a reporter yeast strain is used that contains a recombinant reporter construct comprising a DNA sequence element recognized by a DNA binding domain, operatively linked to a reporter gene. The yeast strain is transfected with constructs encoding two different hybrid or fusion proteins: 1) a fusion protein comprising the DNA binding domain ("BD") that recognizes the DNA binding sequence element linked to the reporter gene and a target or "bait" protein domain; and 2) a fusion protein comprising a transcriptional activation domain (AD) and a potential interaction partner or "prey" domain. Depending upon the purpose of the assay, prey domains may be known, or alternatively, may be unknown sequences represented in a library. An in vivo interaction of the target and prey domains of the fusion proteins serves to bring the AD together with the BD such that binding of the BD fusion to its DNA binding sequence element on the reporter permits transactivation and expression of the reporter gene.

The two-hybrid assay may be used to identify novel protein binding partners, or, alternatively, may be used to screen for agents that modify the interaction of known interaction partners.

To isolate novel proteins that would affect the ERK kinase cascade, the Raf-1 kinase domain, BXB (Bruder et al., 1992, Genes Dev. 6: 545–556), was used as bait in a yeast two-hybrid screen. The screening of 500,000 clones of a human T-cell library yielded 9 clones that specifically interacted with BXB. Five clones corresponded to 14-3-3 proteins. One clone, termed RKIP, bound to both kinase-active and kinase-negative BXB, but not to control baits as shown in FIG. 2(a). The binding of RKIP to proteins of the Raf/MEK/ERK signal transduction pathway was further investigated using an RKIP-GST fusion protein in in vitro association/pull down assays. The binding of recombinant BXB, full-length Raf-1, MEK-1 and ERK-2 to RKIP-GST is shown in FIG. 2(b).

A quantification of Raf-1, MEK, ERK and RKIP protein levels in the cell lines used in this study showed a wide variation of RKIP expression relative to the kinases. The ratio between Raf-1:MEK:ERK:RKIP was: 1:1.6:2.4:14 in Rat-1 cells, 1:1.4:3.5:27 in 208F cells; 1:0.7:9:4.2 in NIH3T3 cells; and 1:2.9:5.9:<1.9 in COS-1 cells. Thus, in at least three fibroblast cell lines, RKIP is abundant enough to be stoichiometrically relevant as an inhibitor.

Figure 2D:
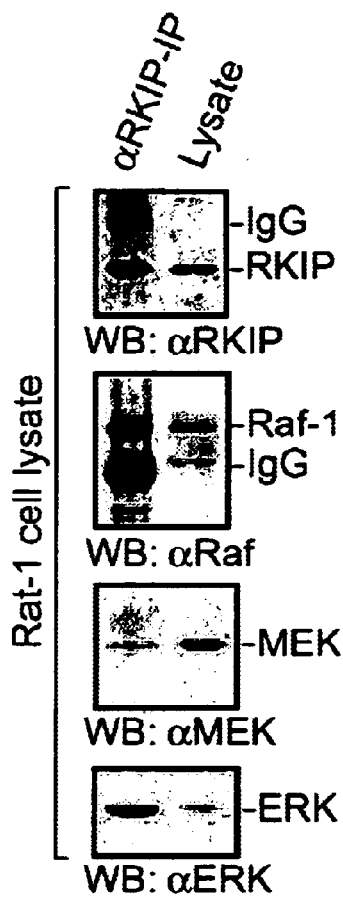
FIG. 2 shows in vitro interaction of RKIP with components of the ERK pathway. a) RKIP interacts with BXB, but not control baits in the yeast two hybrid system. b) Binding of recombinant BXB, full-length Raf-1, MEK-1 and ERK-2 to GST-RKIP beads. "Input", 1% of the respective proteins used in binding reactions; "GST", GST-beads. c) Co-immunoprecipitation of RAF-1, MEK and ERK with RKIP in Rat-1 cells. The RKIP aritiserum does not precipitate recombinant Raf-1, MEK-1 and ERK-2 proteins individually. d) Co-localization of Raf-1 and RKIP in 208F fibroblasts by confocal microscopy. "Antigen competition", antisera were pre-absorbed with their cognate antigens.
Figure 2E:
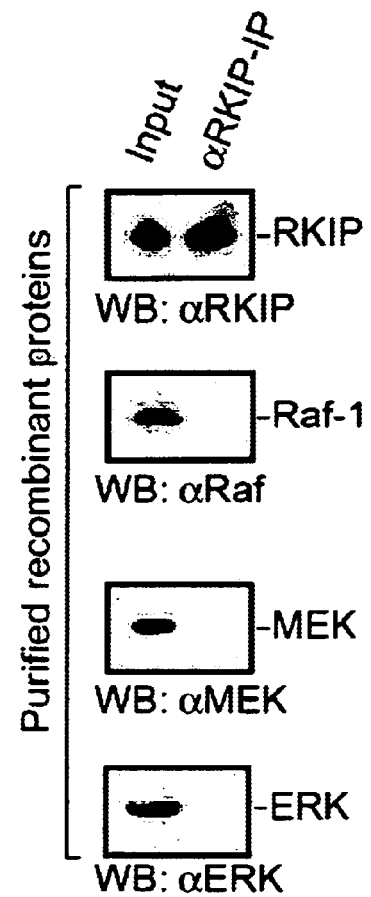
Figure 2F:
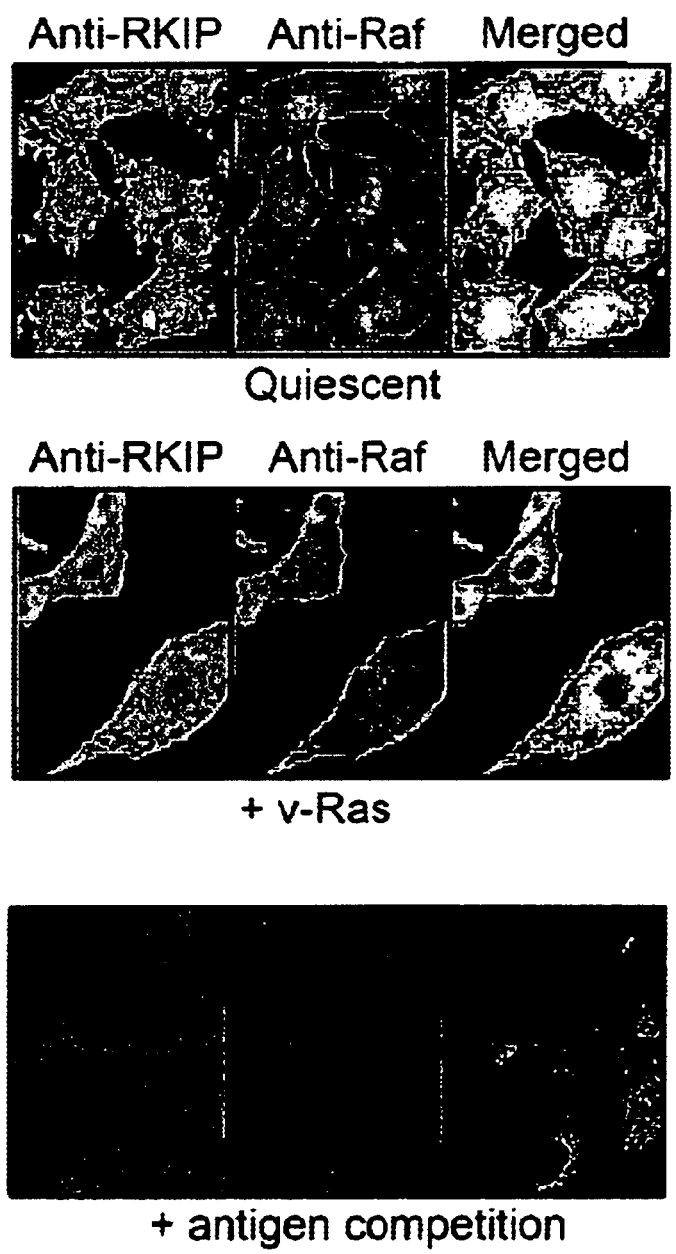

RKIP also co-localized with Raf-1 in Ras-transformed cells shown in FIG. 2(d), suggesting that an appreciable fraction of Raf-1 and its inhibitor RKIP remain associated even under conditions which promote Raf-1 activation. This explains an observation that only a small fraction of Raf-1 can be activated (Hallberg et al., 1994, J. Biol. Chem. 269: 3913–3916).

2. The RKIP Family

Partial sequencing of the RKIP cDNA predicted a protein identical to the 23 kDa phosphatidylethanolamine binding proteins (PEBP) from humans and monkeys. These proteins are widely expressed and evolutionarily conserved, but until the present invention their function has remained obscure. The RKIP amino acid sequence was aligned with PEBP homologs from several species. This alignment resulted in the identification of an RKIP motif that is well conserved across the metazoan species including mammals, flies and worms. The motif also shows considerable conservation in plants and yeasts.

The RKIP motif is a phosphoryl binding pocket comprising the consensus amino acid sequence.

$TLX_3DPD(Z)PX_3(B)X_4EX_2H\_YX_4PX_{(2-4)}GXHR(O)VX(Z)X_3Q$ (SEQ ID NO:1) wherein the single letter amino acid code is in accordance with the IUB/IUPAC code, Z indicates a hydrophobic amino acid residue, B indicates a negatively charged amino acid residue (D or E), and O indicates an aromatic amino acid residue (Y or F). In members of the RKIP family, this motif is comprised within a structure comprising a characteristic β-fold formed by two antiparallel β-sheets. The characteristic β-fold structure forms a small cavity. Mutagenesis of conserved residues in the cavity or pocket region resulted in loss of the ability of RKIP to interact with Raf-1, loss of Raf-1 inhibitory activity and loss of biological activity in vivo. The pocket region, referred to herein as the "phosphoryl binding pocket" is thus identified as important in the inhibitory function of RKIP and RKIP family members. In addition to effects on the Raf/MEK/ERK pathway, RKIP has been found to inhibit kinases in the NF-κB-mediated signal transduction pathway, including NIK and TAK. The binding and inhibition of kinases in these separate pathways demonstrates that RKIP family members can influence diverse signal transduction pathways.

3. Nucleic Acid Encoding an RKIP Motif

The sequence of human RKIP gene is identical to that of the human PEBP gene (GenBank Accession Nos.: S76773, X75252 and X85033 (human); U43206 (mouse); X73137, X75253, X75254, X71873 (monkey). The RKIP motif of the human RKIP gene is encoded by a nucleic acid with the sequence (nucleotides 51–240 of the sequence provided in GenBank ID No. S76773):

5'-ACCTTGGTCCTGACAGACCCGGATGCTCCC AGCAGGAAG GATCCCAAATACAGAGAATG-GCATCATTTCCTGGTGGTCA ACAT-GAAGGGCAATGACATCAGCAGTGGCA-CAGTCCTCTC CGATTATGTGGGCTCGGGGCCTC-CCAAGGGCACAGGCCTC CACCGCTATGTCTGGCTGGTTTACGAGCAG-3' (SEQ ID NO: 11)

A clone encoding an RKIP motif or an RKIP family member protein may be isolated from a cDNA library. Techniques for producing and probing nucleic acid sequence libraries are described, for example, in Sambrook et al., "Molecular Cloning: A Laboratory Manual" (New York, Cold Spring Harbor Laboratory, 1989). In order to isolate a cDNA for human RKIP, one may perform RT-PCR with primers selected from the published PEBP sequence. RKIP clones are also available upon request from the laboratories in which they were cloned (see GenBank listings).

An RKIP family member cDNA can be prepared either by low-stringency probing of a library with a probe derived from the RKIP gene or by probing a cDNA library with a degenerate oligonucleotide (or more correctly, collection of oligonucleotides) designed from the RKIP motif The preparation and use of degenerate oligonucleotide sequences for the identification of cDNAs is well known in the art, as is low stringency probing with a known cDNA sequence. Alternatively, an expression library, prepared in, for example, λGT11 or another protein display vector system can be probed with an antibody that recognizes an RKIP motif Antibodies recognizing an RKIP motif may be raised by one of skill in the art using synthetic peptides derived from the consensus sequence as an immunogen.

After the cloning of a family member according to methods described above, an isolated nucleic acid encoding a given RKIP motif may be prepared by direct synthesis of the sequence encoding the consensus amino acid sequence, or, alternatively, by PCR using primers that hybridize to the sequence encoding the consensus amino acid motif and a cDNA template. This applies to an isolated nucleic acid sequence comprising sequence encoding an RKIP motif and to an isolated nucleic acid sequence consisting essentially of sequences encoding an RKIP motif.

An isolated sequence consisting essentially of an RKIP motif-encoding sequence may be cloned into a vector for expression as is (i.e., as a stand-alone RKIP motif polypeptide), or it may be fused to any of a number of carrier proteins known in the art for expression (e.g., GST). In either case, such cloning generates a vector sequence operatively linked to a nucleic acid "cassette" sequence encoding an amino acid sequence consisting essentially of an RKIP motif. Carrier sequences may confer additional useful characteristics, such as membrane binding or localization, upon the RKIP motif.

B. Identifying Agents that Modulate the Activity of RKIP Motif-containing Proteins In the following discussion, and throughout this specification, it should be understood that methods using RKIP or the RKIP motif identified herein apply equally to all members of the RKIP family.

The influence of RKIP over signal transduction events in diverse pathways makes it a strong target for the modulation of those pathways, and thereby, the modulation of the physical manifestations of those pathways. For example, the Raf/MEK/ERK pathway is involved in the regulation of cell proliferation, and the NF-κB transcription factor pathway is involved in the regulation of cell proliferation, apoptosis and immune functions, including but not limited to inflammation. The identification of RKIP and the RKIP family as regulators of kinases involved in these pathways highlights the usefulness of agents that modify the activities of RKIP family members in the treatment or prevention of diseases or disorders involving these pathways.

Agents that modify the activities of RKIP family members include those that inhibit RKIP activity and those that enhance RKIP activity. An important subset of agents that enhance RKIP activity are those agents that mimic RKIP activity (It is noted that mimics of RKIP activity include peptide sequences consisting essentially of an RKIP motif as defined herein). Agents that enhance or mimic RKIP activity may be used, for example, to inhibit cell proliferation induced by activation of the Raf/MEK/ERK pathways. Such agents are useful in the treatment of cell proliferative disorders, including but not limited to cancer. Alternatively, agents that inhibit the activity of RKIP family members may be useful, for example, to block inflammation or apoptotic cell death by blocking or modifying the activation of NF-κB. Methods are described below for identifying agents that interact with RKIP family members and/or modify the activities of RKIP family members. Agents include but are not limited to polypeptides, peptides, nucleic acids, and small molecules.

I. Identifying Polypeptides that Interact with RKIP Motif-containing Proteins.

In one embodiment, the present invention provides a method of identifying an agent which modulates cell growth. In one embodiment the modulation is detected by detecting an agent which binds an RKIP motif. In other embodiments, modulation is detected by disruption of or competition for binding of an RKIP motif-containing polypeptide to a known binding partner.

A subset of agents according to the invention is polypeptides. An RKIP polypeptide or a fragment comprising an RKIP motif may be used to identify polypeptides that bind the RKIP motif. Methods useful for the identification of such polypeptides include, for example, yeast two-hybrid assays, and pull-down assays using reagents that specifically bind a target protein.

a. Yeast Two-hybrid Assays.

The yeast two-hybrid assay has been described herein above and is well known in the art. To apply this assay format to the identification of polypeptides that bind RKIP motifs, an RKIP motif is used as "bait", and a library or other source of candidate clones supplies the "prey". The generation of a positive reporter signal by a clone identifies that clone as containing a prey protein that interacts with an RKIP motif. That protein may then be characterized to determine whether it inhibits or activates pathways determined to be RKIP sensitive. Further, one of skill in the art may use the two-hybrid method or other methods known in the art or described herein to determine the region or regions of a newly identified RKIP interaction partner that are necessary for interaction with RKIP. The two-hybrid assay therefore permits the identification of RKIP binding partners or kinase inhibition targets from any signal transduction pathway. Partners so identified (whether previously known in the art or novel proteins) may be characterized with respect to kinase activity, modulation of that kinase activity by RKIP family members, and the ultimate modulation of downstream gene expression using methods described herein or known in the art.

b. Pull-down Assays.

Assays based on the specific recognition and precipitation of a given target protein may be used to identify the presence of RKIP interacting proteins. There are two common approaches to this. In the first, antibodies or the binding fragments thereof (e.g., Fv fragments) that recognize an RKIP polypeptide are used to precipitate RKIP polypeptide from a sample (e.g., a labeled cell lysate). The precipitated proteins are separated on a gel and the label is detected, revealing the presence of cellular proteins that co-precipitate with the RKIP polypeptide. Microsequencing of the proteins in the labeled bands can be used to identify the binding proteins if desired. As an alternative to labeling the lysate, the proteins precipitated by the anti-RKIP antibody may be detected by probing separated proteins with specific antibodies for known or suspected RKIP-interacting polypeptides. This approach has the advantage of directly identifying the protein that bound the RKIP polypeptide or motif.

The second common approach is to express the protein of interest (e.g., RKIP) as a fusion with a recognizable tag that permits specific precipitation. Commonly used tags include, but are not limited to glutathione-S-transferase (GST, which binds glutathione on solid supports), hexa-histidine (His, or 6x-His, which binds nickel on solid supports), Flag (an antibody to a specific peptide), maltose binding protein (MBP, which binds maltose on solid supports), and Myc (a peptide from the c-Myc proto-oncoprotein, recognized by anti-Myc antibodies). Vectors for the expression of cloned genes as tagged fusions are well known in the art. In order to identify polypeptides that bind RKIP or RKIP motif-containing proteins, one may first overexpress a tagged RKIP fusion protein, preferably, but not necessarily in bacteria. The tagged polypeptides are harvested using affinity beads bearing the tag-specific binding moiety. Beads are then incubated with cell lysates in a manner similar to the antibody-mediated method described above. Lysates may be labeled or unlabeled. Bound protein:tagged RKIP complexes are washed extensively and specifically bound complexes are electrophoresed on SDS polyacrylamide gels and visualized either by label detection or by probing with antibodies for suspected binding partners. As with the antibody-mediated method described above, microsequencing of the separated proteins may be used to identify or characterize the RKIP binding partners.

Other methods include, for example, in vitro and in vivo reporter assays using transcriptional control elements from genes ultimately regulated by RKIP-modulated pathways, and methods that directly monitor binding of proteins or other agents to RKIP motifs, such as surface plasmon resonance and fluorescence polarization. These additional methods are described in the following sections relating to assays for agents (polypeptide or non-polypeptide) that modulate RKIP activity.

2. Assays for Agents that Modulate RKIP Family Member Activity.

Agents that modulate RKIP family member activity may be identified in a number of ways, but these methods may generally be divided into two categories: 1) those that directly monitor binding to RKIP; and 2) those that monitor one or more functions of RKIP. Methods that monitor binding include, for example, surface plasmon resonance, fluorescence polarization, scintillation proximity assays, fluorescence resonance energy transfer (FRET), modified pull-down based assays, and yeast two-hybrid based assays. Methods that monitor functional aspects of RKIP include in vitro or in vivo transcriptional reporter assays, kinase activation assays and transformation assays.

a. Assays Based on Direct Binding.

i. Surface Plasmon Resonance.

The technique of surface plasmon resonance is well-suited for the screening of candidate compounds for direct binding to a given molecule, or for the identification of compounds that disrupt the binding of a known binding partner. The method, also referred to as the BIAcore system, was developed by Pharmacia Biosensor and is described in the equipment manufacturer's instructions (LKB Pharmacia, Sweden). The BIAcore system or its substantial equivalent uses an affinity purified anti-GST antibody to immobilize GST-fusion proteins onto a sensor chip. Obviously, other fusion proteins and corresponding antibodies may be substituted. The sensor utilizes surface plasmon resonance, which is an optical phenomenon that detects changes in refractive indices. In one form, a homogenate of a tissue or other sample of interest is passed over the immobilized fusion protein and protein-protein or other interactions with the immobilized fusion protein are registered as changes in the refractive index. The system determines binding and the kinetics of that binding. When coupled with mass spectrometry, surface plasmon resonance can identify compounds that bind a given protein based on the unique mass spectra of such compounds.

An RKIP-containing fusion protein similar or identical to the RKIP-GST fusion protein described herein is used in the assay. The sensor chip may be used to measure binding of candidate agents directly to RKIP, which provides information on the affinity of binding of those agents. Binding agents identified in this manner will then be analyzed for their effect on RKIP activity using other approaches as described herein. Alternatively, the effect of an agent on a pre-formed RKIP-motif:partner complex (e.g., RKIP:Raf-1) may be measured as a change in resonance of the complex. In this case, one obtains information not only on the binding of the agent, but on the ability of the agent to disrupt the RKIP:partner interaction. The process is fast and simple, and recent advances in the technique (e.g., adaptation to arrays of proteins) are making high throughput screening of agents easier.

ii. Fluorescence Resonance Energy Transfer (FRET)

Another method of measuring the modulation of binding of two proteins uses fluorescence resonance energy transfer, or FRET (Wu and Brand, 1994, Anal. Biochem. 218:1–13; Lakey, 1993, J. Mol. Biol. 230: 1055–1067). FRET is a quantum mechanical phenomenon that occurs between a fluorescence donor (D) and a fluorescence acceptor (A) in close proximity (usually<100 A of separation.) if the emission spectrum of D overlaps with the excitation spectrum of A. In this situation, when the fluorescence donor is stimulated to emit fluorescence the emitted light stimulates fluorescence of the acceptor fluorophore. The emission from the acceptor is at a different wavelength than that of the donor, and the excitation spectrum of the donor is such that the excitation wavelength used to excite the donor does not directly stimulate the acceptor. Therefore, FRET is evidenced by the emission at the acceptor's emission spectrum when the excitation wavelength is only able to stimulate the donor. Because energy transfer can only occur when labeled proteins or other molecules are in close proximity, a decrease in FRET results when the binding partners are separated by the interaction with a candidate agent. Methods for labeling binding partners with donor/acceptor pairs will vary with the nature of the fluorophores, and are well known in the art. Exemplary donor/acceptor pairs include: FITC-Rhodamine; FITC-CY3; and ALEXA488-Rhodamine.

Further, fluorescent proteins, such as GFP and variants of it may be expressed as fusion proteins with the RKIP and known interaction partner proteins. The co-expression of fusion proteins capable of FRET permits the monitoring of protein-protein interactions in vivo in real time. Variants of Aeqourea victoria GFP exist, for example, that allow FRET (see, for example, Prasher, D. C., et al., Gene, 111:229–233 (1992); Heim, R., et al., Proc. Natl. Acad. Sci., USA, 91:12501–04 (1994); Heim, R. & Tsien, R. Y. Current Biol. 6:178–182 (1996); Tsien, R. Y., et al., Trends Cell Biol. 3:242–245 (1993); U.S. Pat. No. 5,625,048; U. S. Pat. No. 6,054,321; and International application PCT/US95/14692, filed Nov. 10, 1995. For example a blue-shifted GFP mutant P4-3 (Y66H/Y145F) and an improved green mutant S65T can respectively serve as a donor and an acceptor for fluorescence resonance energy transfer (Tsien, R. Y., et al., 1993, supra). Other combinations of GFP variants include, for example: BFP-GFP; BFP-YFP; CFP-YFP; BFP-dsRED; GFP-dSRED; CFP-dsRED; and YFP-dsRED.

In addition to FRET, another related fluorescence-based assay uses a fluorophore and a quencher of fluorescence from that fluorophore as labels on separate members of a binding or interacting pair. When the members of the pair are in close proximity (i.e., bound to each other), fluorescence is quenched. Disruption of the binding results in separation of the quencher from the fluorophore and detection of fluorescence. This has been adapted to monitor protein:protein and protein:nucleic acid interactions and may be used to investigate interactions of RKIP family members with target kinases and with candidate modulator agents. Appropriate fluorophore:quencher pairs are known to those of skill in the art.

iii. Fluorescence polarization

In addition to the surface plasmon resonance and FRET methods, fluorescence polarization measurement is useful to quantitate protein-protein binding.

The fluorescence polarization value for a fluorescently-tagged molecule depends on the rotational correlation time or tumbling rate. Protein complexes, such as those formed by an RKIP motif-containing polypeptide associating with a fluorescently labeled polypeptide (e.g., a known RKIP binding partner or the binding fragment thereof, such as a kinase in a signal transduction pathway), have higher polarization values than a fluorescently labeled monomeric protein. Inclusion of a candidate inhibitor of the RKIP motif:partner interaction results in a decrease in fluorescence polarization relative to a mixture without candidate inhibitor if the candidate inhibitor disrupts or inhibits the interaction of an RKIP motif with its polypeptide binding partner. It is preferred that this method be used to characterize small molecules that disrupt polypeptide complexes.

iv. Scintillation Proximity Assay

A scintillation proximity assay may be used to characterize the interaction between an association of an RKIP motif-containing polypeptide and another polypeptide. An RKIP motif-containing polypeptide can be coupled to beads containing a scintillant (i.e., a compound that emits detectable light when it absorbs a radioactive decay particle). The addition of radiolabeled binding partner results in binding where the radioactive source molecule is in close proximity to the scintillation fluid, which allows scintillation. Thus, compounds that prevent the association of the binding pair result in diminished scintillation signal.

v. Modified Pull-down Assays.

The pull-down assays described herein above may be adapted for use in screening for agents that modify the binding of an RKIP motif to a known partner. Essentially, one would perform such an assay by mixing a tagged RKIP polypeptide and a known interaction partner in the presence and absence of a candidate agent and then monitoring the relative amount of the known partner that is pulled down with the tagged RKIP. A decrease in the pull-down of the known partner is indicative of an agent's inhibition or destabilization of the interaction, while an increase in pull-down is indicative of an agent's promotion/stabilization of the interaction. Performing the assay under conditions of excess known interaction partner will generally allow one to identify both inhibitors and enhancers of the interaction.

vi. Yeast two-hybrid assays.

In addition to their use for identifying novel interaction partners for the RKIP motif, yeast two-hybrid assays may also be used to screen for agents that modify the interaction of RKIP proteins with proteins of the signal transduction pathway one wishes to modulate. In this instance, a known interaction partner, for example Raf-1 is used as "prey" and an RKIP family member or RKIP motif is used as "bait". In the absence of an RKIP activity modifying agent, the co-transfection of both bait and prey constructs into a reporter strain of yeast results in reporter activity. For the purpose of this discussion, this situation is referred to as an "active two-hybrid system". In order to assay for agents that modify the interaction of an RKIP motif with its binding partner, one then treats yeast cells containing an active two-hybrid system with candidate agents and monitors the reporter activity. A decrease in reporter activity is indicative that a candidate agent interferes with the interaction of the RKIP motif with the known interaction partner. Conversely, an increase in activity is indicative of enhanced interaction caused by the candidate agent.

Controls for the two-hybrid agent-screening method may be designed by one of skill in the art, but may include, for example, a yeast strain in which the activation domain and DNA binding domain normally separated in the two-hybrid format are expressed as a single protein. That is, where the reporter is dependent upon the reconstitution of, for example, Gal4 activity, a strain carrying intact Gal4 trans-activator and reporter without RKIP or partner fusions should be treated with the same candidate agents. This control allows the discrimination of agents that specifically modify the interaction of the RKIP with the interaction partner from those that generally alter the expression of the reporter or the health of the cell.

b. Assays Based on Functional Aspects of RKIP Family Members.

i. Transcription assays.

RKIP is known to modulate signal transduction pathways including those involving Raf/MEK/ERK and NF-κB family members (e.g., NIK and TAK). These pathways ultimately lead to the modification of the expression of specific genes. Therefore, one may use genes ultimately regulated by these pathways to identify modulators of RKIP family activity. To do this, sequences responsive to a given pathway are operatively linked to a reporter gene (e.g., β-gal, GFP, luciferase, CAT, etc.) to generate a reporter construct. The reporter construct is then introduced to eukaryotic host cells, including for example, insect or mammalian cells, and preferably human cells. The reporter is preferably, but not necessarily, stably integrated into the genome of the host cells. These reporter cells are treated with candidate agents and the expression of reporter is measured. An increase or decrease in reporter expression in the presence, as compared to the absence of an agent is indicative of an effect of that agent on the RKIP-modulated pathway. It should be noted that reporter assays may also be performed in a cell-free manner using nuclear extracts capable of supporting transcription.

Examples of transcriptional control elements that are responsive to changes in RKIP activity include, but are not limited to those responsive to the AP-1 transcription factor and those responsive to NF-κB activity. The consensus AP-1 binding site is the palindrome TGA(C/G)TCA (SEQ ID NO:10)(Lee et al., 1987, *Nature* 325: 368–372; Lee et al., 1987, *Cell* 49: 741–752). The AP-1 site is also responsible for mediating induction by tumor promoters such as the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC(SEQ ID NO11). For a non-limiting listing of NF-κB responsive genes, the control elements of which may be used to make NF-κB responsive reporter constructs, see Table 1. Vectors encoding NF-κB responsive reporters are known in the art or can be readily made by one of skill in the art. Further, NF-κB responsive reporters are commercially available from, for example, CLONTECH.

TABLE 1

TARGET GENES OF NF-κB

| Gene | Function | Reference |
|---|---|---|
| Cytokines/Chemokines and their modulators | | |
| CINC | Cytokine-induced neutrophil chemoattractant | Blackwell et al., 1994 Ohtsuka et al., 1996 |
| *CXCL 11 | Chemokine ligand for CXCR3 | Tensen et al., 1999 |
| Eotaxin | β Chemokine, eosinphil-specific | Hein et al., 1997 |
| Gro a-y | Melanoma growth stimulating activity | Anisowicz et al., 1991 |
| IFN-y | Interferon | Sica et al., 1992; Sica et al., 1997 |
| IL-1a | Interleukin-1a | Mori and Prager, 1996 |
| IL-1β | Interleukin-1b | Hiscott et al., 1993 |
| IL-1-receptor antagonist | Inhibitor of IL-1 activity | Smith et al., 1994 |
| IL-2 | Interleukin-2 | Serfling et al., 1989; Hoyos et al., 1989; Lai et al., 1995 |
| IL-6 | Interleukin-6, inflammatory cytokine | Libermann and Baltimore, 1990; Shimizu et al., 1990 |
| IL-8 | Interleukin-8, a-chemokine | Kunsch and Rosen, 1993 |
| *IL-9 | Interleukin-9 | Zhu et al., 1996a |
| IL-11 | Interleukin-11 | Bitko et al., 1997 |
| IL-12 (p40) | Interleukin-12 | Murphy et al., 1995 |
| *IL-15 | Interleukin-15 | Azimi et al., 1998 |
| β-Interferon | Interferon | Hiscott et al., 1989; Lenardo et al., 1989 |
| IP-10 | a Chemokine | Ohmori and Hamilton, 1993 |
| KC | a Chemokine | Ohmori et al., 1995 |
| Lymphotoxin a | | Worm et al., 1998 |
| Lymphotoxin β | Anchors TNF to cell surface | Kuprash et al., 1996 |
| MCP-1/JE | Macrophage chemotactic protein, b Chemokine | Ueda et al., 1994 |
| MIP-1a, β | Macrophage inflammatory protein-1, b Chemokine | Grove and Plumbi, 1993; Widmer et al., 1993 |
| MIP-2 | Macrophage inflammatory protein-1, b Chemokine | Widmer et al., 1993 |
| RANTES | Regulated upon Activation Normal T lymphocyte Expressed and Secreted, β Chemokine | Moriuchi et al., 1997 |
| TCA3, T-cell activation gene 3 | T-cell activation gene 3, β Chemokine | Oh and Metcalfe, 1994 |
| TNFa | Tumor necrosis factor a | Shakhov et al., 1990; Collart et al., 1990 |
| TNFβ | Tumor necrosis factor b | Paul et al., 1990; Messer et al., 1990 |
| Immunoreceptors | | |
| B7.1 (CD80) | Co-stimulation of T cells via CD28 binding | Fong et al., 1996; Zhao et al., 1996 |
| BRL-1 | B-cell homing receptor | Wolf et al., 1998 |
| CCR5 | Chemokine receptor | Liu et al., 1998 |
| CD48 | Antigen of stimulated lymphocytes | Klaman and Thorley-Lawson, 1995 |
| $F_c$ epsilon receptor II (CD23) | Receptor for IgE | Richards and Katz, 1997 |

TABLE 1-continued

TARGET GENES OF NF-κB

| Gene | Function | Reference |
| --- | --- | --- |
| IL-2 receptor a-chain | IL-2 receptor subunit | Ballard et al., 1988 |
| Immunoglobulin Cgammal | IgG heavy chaini | Lin and Stavnezer, 1996 |
| Immunoglobulin e heavy chain | IgE heavy chain | Iciek et al., 1997 |
| Immunoglobulin k light chain | Antibody light chain | Sen and Baltimore, 1986b |
| Invariant Chain $I_1$ | Antigen presentation | Pessara and Koch, 1990 |
| MHC class I (H-2K$^b$) | Mouse histocompatibility antigen | Israel et al., 1989a; Israel et al., 1989b |
| MHC Class I HLA-B7 | Mouse histocompatibility antigen | (Johnson and Pober, 1994) |
| β2 Microglobulin | Binds MHC class I | Israel et al., 1989a; Israel et al., 1989b |
| T-cell receptor β chain | T-cell receptor subunit | Jamieson et al., 1989 |
| *TNF-Receptor, p75/80 | High-affinity TNF receptor | Santee and Owen-Schaub, 1996 |
| | Proteins involved in antigen presentation | |
| Proteasome Subunit LMP2 | Subunit of 26S proteasome, cysteine protease | Wright et al., 1995 |
| Peptide Transporter TAP 1 | Peptide transporter for ER | Wright et al., 1995 |
| | Cell adhesion molecules | |
| ELAM-1 | E-selectin, endothelial cell leukocyte adhesion molecule | Whelan et al., 1991 |
| ICAM-1 | Intracellular adhesion molecule-1 | van de Stolpe et al., 1994 |
| MadCAM-1 | Mucosal addressin cell adhesion molecule | Takeuchi and Baichwal, 1995 |
| P-selectin | Platelet adhesion receptor | Pan and McEver, 1995 |
| Tenascin-C | ECM protein controls cell attachment and migration, cell growth | Mettouchi et al., 1997 |
| VCAM-1 | Vascular cell adhesion molecule | Iademarco et al., 1992 |
| | Acute phase proteins | |
| Angiotensinogen | Angiotensin precursor, regulates blood pressure | Brasier et al., 1990; Ron et al., 1990 |
| C4b binding protein | Complement binding protein | Moffat and Tack, 1992 |
| Complement factor B | Complement factor | Nonaka and Huang, 1990 |
| Complement Factor C4 | Activates extrinsic pathway of complement activation | Yu et al., 1989 |
| C-reactive protein | Pentraxin | Zhang et al., 1995 |
| Lipopolysaccharide binding protein | Binds to LPS receptor (CD14) with LPS | Schumann, 1995 |
| Pentraxin PTX3 | Pentraxin | Basile et al., 1997 |
| Serum amyloid A precursor | Serum component | Edbrooke et al., 1991; Li and Liao, 1991 |
| Tissue factor-1 | Activates extrinsic pathway of complement activation | Mackman et al., 1991 |
| Urokinase-type Plasminogen activator | Activates fibrinogen for fibrin clot lysis | Novak et al., 1991 |
| | Stress response genes | |
| Angiotensin II | Peptide hormone | Brasier et al., 1990 |
| COX-2 | Cyclooxygenase, prostaglandin endoperoxide synthase | Yamamoto et al., 1995 |
| Ferritin H chain | Iron storage protein | Kwak et al., 1995 |
| *5-Lipoxygenase | Arachidonic acid metabolic enzyme, leukotriene synthesis | Chopra et al., 1992 |
| 12-Lipoxygenase | Arachidonic acid metabolic enzyme | Arakawa et al., 1995 |
| inducible NO-Synthase | NO synthesis | Geller et al., 1993 |
| Mn SOD | Superoxide dismutase | Das et al., 1995 |
| NAD(P)H quinone oxidoreductase (DT-diaphorase) | Bioreductive enzyme | Yao and O'Dwyer, 1995 |
| Phospholipase A2 | Fatty acid metabolism | Morri et al., 1994 |
| | Cell-surface receptors | |
| A1 adenosine receptor | Pleiotropic physiological effects | Nie et al., 1998 |
| Bradikinin B1-Receptor | Pleiotropic physiological effects | Ni et al., 1998 |
| *CD23 | Cell-surface molecule | Tinnell et al., 1998 |
| CD69 | Lectin mainly on activated T cells | Lopez-Cabrera et al., 1995 |
| Gal1 Receptor | Galanine receptor, neuroendocrine peptide | Lorimer et al., 1997 |
| Lox-1 | Receptor for Oxidized low density lipoprotein | Nagase et al., 1998 |
| Mdr1 | Multiple drug resistance mediator (P-glycoprotein) | Zhou and Kuo, 1997 |
| Neuropeptide Y Y1-receptor | Pleiotropic physiological effects | Musso et al., 1997 |
| PAF receptor 1 | Platelet activator receptor | Mutoh et al., 1994 |

TABLE 1-continued

TARGET GENES OF NF-κB

| Gene | Function | Reference |
|---|---|---|
| RAGE- receptor for advanced glycation end products | Receptor for Advanced Glycation End products | Li and Schmidt, 1997 |
| *Regulators of apoptosis* | | |
| Bfl1/A1 | Pro-survival Bcl-2 homologue | Grumont et al., 1999; Zong et al., 1999 |
| Bcl-xL | Pro-survival Bcl-2 homologue | Chen et al., 1999; Lee et al., 1999b |
| Nr13 | Pro-survival Bcl-2 homologue | Lee et al., 1999c |
| CD95 (Fas) | Pro-apoptotic receptor | Chan et al., 1999 |
| Fas-Ligand | Inducer of apoptosis | Matsui et al., 1998 |
| IAPs | Inhibitors of Apoptosis | You et al., 1997; Stehlik et al., 1998 |
| IEX-1L | Immediate early gene | Wu et al., 1998 |
| *Growth factors and their modulators* | | |
| G-CSF | Granulocyte Colony Stimulating Factor | Nishizawa and Nagata, 1990 |
| GM-CSF | Granulocyte Macrophage Colony Stimulating Factor | Schreck and Baeuerle, 1990 |
| *IGFBP-1 | Insulin-like growth factor binding protein-1 | Lang et al., 1999 |
| IGFBP-2 | insulin-like growth factor binding protein-2 | Cazals et al., 1999 |
| M-CSF (CSF-1) | Macrophage Colony Stimulating Factor | Brach et al., 1991b |
| PDGF B chain | Platelet-Derived Growth Factor | Khachigian et al., 1995 |
| Proenkephalin | Hormone | Rattner et al., 1991 |
| *Thrombospondin | Matrix glycoprotein t | Adolph et al., 1997 |
| VEGF C | Vascular Endothelial Growth Factor | Chilov et al., 1997 |
| *Early response genes* | | |
| p22/PRG1 | Rat homology of IEX | Schafer et al., 1998 |
| *p62 | Non-proteasomal multi-ubiquitin chain binding protein | Vadlamudi and Shin, 1998 |
| *Transcription factors* | | |
| A20 | TNF-inducible zinc finger | Krikos et al., 1992 |
| c-myb | Proto-oncogene | Toth et al., 1995 |
| c-myc | Proto-oncogene | Duyao et al., 1992 |
| c-rel | Proto-oncogene | Hannink and Temin, 1990 |
| IRF-1 | Interferon regulatory factor-1 | Harada et al., 1994 |
| IRF-2 | Interferon regulatory factor-2 | Harada et al., 1994 |
| IkB-a | Inhibitor of Rel/NF-kB | Haskill et al., 1991; Sun et al., 1993; DeMartin et al., 1993 |
| junB | Proto-oncogene | Brown et al., 1995 |
| nfkb2 | NF-kB p100 precursor | Lombardi et al., 1995 |
| nfkb1 | NF-kB p105 precursor | Ten et al., 1992 |
| p53 | Tumor suppressor | Wu and Lozano, 1994 |
| *Viruses* | | |
| Adenovirus (E3 region) | Adenovirus | Williams et al., 1990 |
| Avian Leukosis Virus | Causes avian leukosis | Bowers et al., 1996 |
| Bovine Leukemia Virus | Causes bovine leukemia | Brooks et al., 1995 |
| CMV | Cytomegalovirus | Sambucetti et al., 1989 |
| EBV (Wp promoter) | Epstein-Barr virus | Sugano et al., 1997 |
| HIV-1 | Human immunodeficiency virus | Nabel and Baltimore, 1987; Griffin et al., 1989 |
| HSV | Herpes simplex virus | Rong et al., 1992 |
| JC Virus | Polyoma virus | Ranganathan and Khalili, 1993 |
| Measles virus | Causes measles | Harcourt et al., 1999 |
| SIV | Simian immunodeficiency virus | Bellas et al., 1993 |
| SV-40 | Simian virus 40 | Kanno et al., 1989 |
| *Enzymes* | | |
| *Ceramide glycosyl transferase | Glycosphingolipid | Ichikawa et al., 1998 |
| Collagenase 1 | Matrix metalloproteinase | Vincenti et al., 1998 |
| *Dihydrodiol dehydrogenase | Oxidoreductase, oxidation of trans-hydodiols | Ciaccio et al., 1996 |
| *GAD67 | Glutamic acid decarboxylase | Szabo et al., 1996 |
| Gelatinase B | Matrix metalloproteinase | He, 1996 |
| GSTP1-1 | Glutathione transferase | Xia et al., 1996 |
| *Glucosel-6-phosphate dehydrogenase | Hexose monophosphate | Garcia-Nogales et al., 1999 |
| * HO-1 | Hemeoxygenase | Lavrovsky et al., 1994 |
| Hyaluronan synthase | Synthesizes hyaluronic acid | Ohkawa et al., 1999 |

TABLE 1-continued

TARGET GENES OF NF-κB

| Gene | Function | Reference |
|------|----------|-----------|
| Lysozyme | Hydrolyzes bacterial cell walls | Phi van, 1996 |
| Mmp-9, matrix metalloproteinaase-9 | Secreted gelatinase involved in metastasis | Bond et al, 1998; Farina et al, 1999 |
| *PTGIS, prostaglandin synthase | Prostaglandin synthase | Yokoyama et al., 1996 |
| Transglutaminase | Forms isopeptide bonds | Mirza et al., 1997 |
| *Xanthine Oxidase | Oxidative metabolism of purines | Xu et al., 1996 |
| | Miscellaneous | |
| alpha-1 acid glycoprotein | Serum protein | Mejdoubi et al., 1999 |
| Apolipoprotein C III | Apoprotein of HDL | Gruber et al., 1994 |
| *Biglycan | Connective tissue proteoglycan | Ungefroren and Krull, 1996 |
| Cyclin D1 | Cell-cycle regulation | Guttridge et al., 1999; Hinz et al., 1999 |
| *Cyclin D3 | Cell-cycle regulation | Wang et al., 1996b |
| Factor VIII | Hemostasis | Figueiredo and Brownlee, 1995 |
| Galectin 3 | β-galactosidase-binding lectin | Hsu et al., 1996 |
| HMG14 | High mobility group 14 | Walker and Enrietto, 1996 |
| K3 Keratin | Intermiediate filament protein | Wu et al., 1994 |
| Laminin B2 Chain | Basement membrane protein | Richardson et al., 1995 |
| Mts1 | Multiple tumor suppressor | Tulchinsky et al., 1997 |
| *Pax8 | Paired box gene | Okladnova et al., 1997 |
| *UCP-2 | Uncoupling protein-2 | Lee et al., 1999a |
| Vimentin | Intermediate filament protein | Lilienbaum et al., 1990 |
| Wilm's Tumor Supressor Gene | Tumor suppressor | Dehbi et al., 1998 |
| al-antitrypsin | Protease inhibitor | Ray et al., 1995 |

In reporter assays as described above, it may be useful to screen agents in the presence and absence of known activators or inhibitors of the pathway in order to ascertain the point of action of a given agent. For example, an agent may be identified as positively modulating the expression of a reporter construct. If the agent acts by modifying the activity of an RKIP family member or the interaction of an RKIP family member with a member of the pathway of interest, the agent will not overcome inhibition of a known step in the pathway that is "downstream" of the RKIP-modulated step. Alternatively, one may assay the effect of an agent in cells expressing a constitutively active form or a dominant negative mutant of a pathway member. Generally, if an agent acts upstream of that step influenced by a constitutively active pathway member, the agent will not affect the expression of the reporter. A dominant negative mutant will generally not be rescued unless the agent acts downstream of the site of action of the mutant factor. Experiments of this type may be performed whenever a reporter assay identifies a modulating agent in order to determine whether the agent acts on an RKIP activity. Of course, direct assays of kinase activity may also be performed to examine this question. Constitutively active and/or dominant negative mutant pathway members are available in the art for a wide variety of signal transduction factors, including for example, factors involved in the Raf/MEK/ERK and NF-κB-mediated pathways.

ii. Kinase assays.

The phosphorylation of kinase targets may be monitored as a more direct assay for RKIP activity. Because RKIP family members inhibit kinase activity, monitoring the activity of these target kinases in the presence or absence of candidate RKIP modulators permits one to determine the effect of a candidate modulator on RKIP activity. A decrease in RKIP target kinase activity is indicative of increased RKIP activity, while an increase in target kinase activity is indicative of decreased RKIP activity. In vitro kinase assays are performed essentially as described by Haffier et al. (1994, Mol. Cell. Biol. 14: 6696–6703). Briefly, activated RKIP target kinase (e.g., Raf-1) and RKIP are incubated under conditions permitting phosphorylation of a target protein or proteins (e.g., kinase-negative His/MEK), where $\gamma$-$^{32}$P ATP is the source of phosphate, and labeling of the target is measured following immunoprecipitation of kinase target.

iii. Transformation assays.

RKIP activity reduces the transformation of cells in culture by Raf-1 overexpression. This phenomenon may be used to evaluate compounds or agents that modulate the activity of RKIP family members by exposing cells transfected with a Raf expression vector to such agents and monitoring for changes in the number of transformed foci or the time required for the generation of foci in the culture. Other indicators of transformation include morphological transformation and anchorage-independent growth. Agents that increase RKIP activity are expected to reduce focus formation, and agents that decrease RKIP activity are expected to increase focus formation.

c. Mechanism of Action

While not wishing to be bound to any one specific mechanism, we propose that RKIP functions as a rheostat that sets the sensitivity threshold for the activation of the Raf/MEK/ERK pathway. A quantitative analysis of the activation kinetics of the ERK pathway demonstrated that this cascade operates like a switch that suppresses background noise, but strongly amplifies signals exceeding a certain threshold (Ferrel et al. Trends. Biochem. Sci. 21:460–466, 1996). Overexpression of RKIP raises this threshold, whereas downregulation of RKIP lowers it. As both the amplitude, kinetics and overall duration of ERK activity are known to differentiate between biological responses such as cell cycle arrest, transformation, mitogenesis and differentiation (Tombes et al., Biochem. J. 330:1451–1460, 1998; Marshal et al., Cell 80:179–185, 1995; Sewing et al., Mol. Cell. Biol. 17:5588–5597, 1997; Woods et al. Mol Cell Biol., 17:5598–5611, 1997), RKIP will exert a profound influence on these parameters. RKIP may have a similar effect on any signal transduction pathway wherein one or more kinases is bound by an RKIP family protein. An RKIP activity-modulating agent can have an effect on any signal transduction pathway involving an RKIP-sensitive kinase. Non-limiting examples include the Raf/MEK/ERK mediated pathway(s) and the NF-κB-mediated pathways.

d. Candidate Agents

The candidate modulator or candidate agent may be a synthetic compound, a mixture of compounds, or may be a natural product (e.g. a plant extract or culture supernatant).

Candidate agents from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (N.C.), or are readily produceable by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 Daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate agents will be effective at varying concentrations, depending on the nature of the agent and on the nature of its interaction with the RKIP motif or protein bearing the RKIP motif. Therefore, candidate agents should be screened at varying concentrations. Generally, concentrations from about 10 mM to about 1 fM are preferred for screening. The association constants of agents that bind and/or inhibit RKIP family protein activities will generally in the range of about 1 mM to about 1 fM, and optimally in the range of about 1 μM to about 1 pM or less.

An important subset of agents useful for the inhibition of RKIP expression or activity is nucleic acids, particularly antisense nucleic acids directed at the expression of RKIP family mRNAs. As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are typically less efficient inhibitors of translation but could also be used in accordance with the invention. Whether designed to hybridize to the 5', 3', or coding region of subject mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/098 10, published Dec. 15, 1988) or the blood-brain barrier (see, e.g., PCT Publication No. WO 89/10 134, published Apr. 25, 1988), hybridization-triggered cleavage agents (See, e.g., Krol et al., 1988, BioTechniques 6:958–976), or intercalating agents (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Peny-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methyiphosphonate, an alkyl phosphotriester, and a formacetal or analog thereof In yet a further embodiment, the antisense oligonucleotide is an α-anomeric oligonucleotide. An α-anomeric oligonucleotide forms specific double-stranded hybrids with complementary RNA in which, contrary to the usual n-units, the strands run parallel to each other (Gautier et al, 1987, Nucl. Acids Res. 15:6625–6641). The oligonucleotide is a 2'-O-methylribonucleotide (Inoue et al., 1987, Nucl. Acids Res. 15:6131–12148), or a chimeric RNA-DNA analogue (Jnoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209) and methylphosphonate oligonucleotides can be prepared by use of controlled pore glass polymer supports (Sarini et al., 1988, Proc. Natl. Acad. Sci. U.S.A. 85:7448–7451).

C. Diagnostic and Therapeutic Uses of RKIP Motifs and RKIP Family Proteins

In one embodiment, the present invention provides a method of detecting a condition associated with abnormal cell proliferation by determining the amount of RKIP in a tissue sample. Like the ERK pathway, RKIP is widely expressed. A quantification of Raf-1, MEK, ERK and RKIP protein levels in the cell lines shows a wide variation of RKIP expression relative to the kinases. However, for any given cell type, there is a normal level of RKIP family expression. Because RKIP family proteins inhibit signal transduction kinases, and because the inappropriate inactivation or activation of signal transduction pathways is associated with diseases or disorders including, but not limited to cancer and immune dysfunction such as autoimmunity, inflammation and immune deficiency, the levels of RKIP family proteins or even RKIP motifs in general can be used for diagnosis of diseases or disorders. In one embodiment, determination of the amount of RKIP in a tissue sample is performed by measuring the level of expression of a nucleic acid encoding an RKIP motif. In another embodiment, detection is performed by determining the amount of a protein comprising an RKIP motif in a tissue sample.

A diagnostic method based on the detection of nucleic acid encoding an RKIP motif or an RKIP family member protein comprises the steps of obtaining a tissue sample of from an individual, contacting a nucleic acid probe that hybridizes under stringent conditions to a nucleic acid encoding an RKIP motif with mRNA of said tissue sample, and determining the amount of hybridization of the probe. An elevation by at least a factor of 2, at least a factor of 5, at least a factor of 20, or at least a factor of 50 or more in the amount of hybridization with the mRNA of the tissue sample as compared to the amount of hybridization with the mRNA of a standard or control sample is an increase according to the invention. Conversely, a reduction by at least 10%, preferably at least 20%, 35%, 50%, 75% or more, up to and including a 100% decrease (i.e., no signal) is a decrease in hybridization signal according to the invention. A control sample is a tissue sample in which the level of RKIP motif-encoding nucleic acid is within the normal range, which is defined herein as the amount of mRNA encoding a given RKIP family member or RKIP motifs in general in a tissue that is not affected by a cell proliferative disorder, plus or minus about 10%.

An increase in the expression of RKIP motif-containing proteins or the nucleic acids encoding them is indicative of a decreased cell proliferative capacity and/or an increased likelihood or susceptibility to apoptosis, inflammation or other phenomena regulated by an RKIP sensitive pathway. In contrast, a decrease in the expression of such proteins or nucleic acids is indicative of an increased cell proliferative capacity and/or a decreased likelihood or susceptibility to apoptosis, inflammation or other phenomena regulated by an RKIP sensitive pathway. An increase is indicative of a cell proliferative disorder.

In one embodiment, the invention provides a method of detecting the amount of RKIP motif expressed in an individual. For example, the present invention provides methods for determining whether a subject is at risk for developing a disease or condition characterized by abnormal cell proliferation by detecting the disclosed RKIP motif In clinical applications, human tissue samples can be screened for the presence and/or absence of RKIP motif-containing polypeptides or nucleic acids encoding RKIP motifs as identified herein. Such samples could consist of needle biopsy cores, surgical resection samples, lymph node tissue, or serum. For example, these methods include obtaining a biopsy. In certain embodiments, nucleic acids extracted from these samples may be amplified using techniques well known in the art. The level of detected RKIP motif would be compared with statistically valid groups of control tissue samples.

In one embodiment, the diagnostic method comprises determining whether a subject has an abnormal mRNA and/or protein level of the disclosed markers, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the level of RKIP motif encoding mRNA or RKIP motif comprising protein, is determined and compared to the level of RKIP motif encoding mRNA or RKIP motif-comprising protein in a control subject or normal tissue from the same subject. An abnormal level of RKIP motif comprising polypeptide or mRNA levels is indicative of a condition associated with abnormal expression of RKIP motif-containing polypeptides in the individual.

In one aspect, the method comprises in situ hybridization with a probe derived from an RKIP motif encoding nucleic acid. The method comprises contacting the labeled hybridization probe with a sample of a given type of tissue potentially containing abnormally growing cells as well as normal cells, and determining whether the probe labels some cells of the given tissue type to a degree significantly different (increased or decreased) than the degree to which it labels other cells of the same tissue type. A significant difference in RKIP-encoding nucleic acid expression is indicative of a disorder involving an RKIP motif containing protein.

The invention further provides a method of determining whether a cell sample obtained from a subject possesses an abnormal amount of RKIP motif, the method comprising: (a) obtaining a cell sample from the subject; (b) quantitatively determining the amount of the marker polypeptide in the sample so obtained; and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA and the like.

The above diagnostic assays may be carried out using antibodies to detect the level of polypeptides comprising an RKIP motif (either generally or specific RKIP motif-containing polypeptides). In that embodiment, the method comprises the steps of contacting the test tissue with an antibody specific for an RKIP motif that is expressed at a control or standard level in normal tissue of the same tissue type as the test tissue, and determining the amount of immunocomplex formation. A statistically significant difference in the amount of the immunocomplex formed with the RKIP of a test tissue as compared to a normal tissue of the same tissue type is an indication of abnormal cell growth or increased potential for abnormal cell growth or susceptibility to apoptosis or immune dysfunction. In this method and all other diagnostic methods wherein RKIP motif-containing proteins are measured, a difference in RKIP protein levels may be either an increase or a decrease; the level is considered decreased if it is at least 10% lower, 20% lower, 35% lower, 50% lower, 75% lower, 90% lower or even as much as 100% lower (i.e., no RKIP proteins) relative to a standard; the level is considered increased if it is at least two fold higher than in the standard, at least 5 fold, 10-fold, 20-fold or even 50-fold or more higher than standard. An increase or a decrease is indicative of a disorder related to RKIP-sensitive signal transduction. Disorders related to RKIP-sensitive signal transduction include, but are not limited to cancer and other cell proliferative diseases, immunodeficiency, autoimmunity, and inflammation.

Another such method includes the steps of: providing an antibody specific for the RKIP motif, the motif being present in cancerous tissue of a given tissue type at a level more or less than the level of the gene product in abnormal tissue of the same tissue type; obtaining from an individual a first sample of tissue of the given tissue type, which sample potentially includes abnormally growing cells; providing a second sample of tissue of the same tissue type (which may be from the same patient or from a normal control, e.g. another individual or cultured cells), this second sample containing normal cells and essentially no abnormal cells; contacting the antibody with protein (which may be partially purified, in lysed but unfractionated cells, or in situ) of the first and second samples under conditions permitting immunocomplex formation between the antibody and the RKIP motif present in the samples; and comparing (a) the amount of immunocomplex formation in the first sample, with (b) the amount of immunocomplex formation in the second sample, wherein a statistically significant difference (increase or decrease) in the amount of immunocomplex formation in the first sample as compared to the amount of immunocomplex formation in the second sample is indicative of the presence of abnormally growing cells in the first sample of tissue.

Immunoassays are commonly used to quantitate the levels of proteins in cell samples, and many other immunoassay techniques are known in the art. The invention is not limited to a particular assay procedure, and therefore is intended to include both homogeneous and heterogeneous assay procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

Method of Modulating Cell Proliferation According to the Present Invention

In one embodiment, the invention provides a method of modulating cell proliferation by administering to an individual an agent that mimics, enhances or decreases the activity of an RKIP motif-containing polypeptide. Where one wishes to inhibit cell proliferation, an agonist or agent that increases the activity of an RKIP motif-containing polypeptide is preferred. In order to determine whether cells that proliferate in a given cell proliferative disorder are or may be RKIP-sensitive, one may use any of the methods disclosed herein that measure RKIP motif-containing polypeptides and/or the levels of nucleic acids encoding such polypeptides. Alternatively, or in addition, cells from a biopsy may be cultured and assayed for sensitivity to an RKIP activity-modulating agent. A cell is sensitive to an RKIP activity-modulating agent if such an agent results in at least a 20%, and preferably a 35%, 50%, 75%, 100% or 2-fold, 5-fold, 10-fold, 20-fold, 50-fold or greater increase in RKIP motif-containing protein activity relative to that activity detected in the absence of that agent. Alternatively, as would be the case where an agent decreases the activity of an RKIP motif-containing polypeptide, a cell is sensitive to an RKIP activity modulating agent if such agent results in at least a 10%, 20%, 35%, 50%, 75%, 90%, 95% or even up to and including a 100% (no activity) decrease in activity.

In order to modulate cell proliferation, an agent that modulates RKIP motif-containing polypeptide activity, is administered to an individual in need of such treatment. Treatment is considered successful if, for example, the rate of cell proliferation of a cell proliferative disease (as evidenced by, for example, a slowing of the rate of tumor growth, or even a reduction in the size of a tumor) decreases by at least 20%, preferably at least 35%, 50%, 75%, 90%, 95%, or even up to and including 100%. The same guideline applies where treatment is aimed at, for example, modulating the rate of apoptosis or the degree of inflammation. Alternatively, treatment may be monitored by measuring in biopsies the activity of RKIP-sensitive kinases, the level of gene expression regulated by the RKIP-sensitive pathway, or by measuring the levels of RKIP motif-containing protein or the nucleic acids encoding them in the given tissue. The choice of how to monitor will depend in part upon the nature of the agent. For example, an agent that enhances RKIP kinase inhibiting activity may be monitored by monitoring RKIP-sensitive kinase activity in the tissue, while an agent that modulates RKIP expression may be monitored by following that expression.

Method of Modulating Apoptosis According to the Invention

Apoptosis, often referred to as "programmed cell death" or "cell suicide" is a process that has gained attention recently as it has become evident that it plays a role in a number of disease pathologies. Inappropriate programmed cell death has been implicated in, for example, Alzheimer's disease, atherosclerosis, stroke, and dilated cardiomyopathy. In these cases, tissue damage is the result of the inappropriate apoptosis. A failure to undergo apoptosis or to respond to apoptotic stimuli has been implicated in diseases such as cancer and some immune dysfunctions such as inflammatory disorders and autoimmune diseases.

There is evidence, drawn from experiments in which cell lines resistant to apoptosis were rendered sensitive to apoptotic stimuli by the expression of RKIP, that apoptosis is an RKIP-sensitive process (data not shown). Therefore, agents that enhance or mimic the activity of RKIP can be useful in inducing apoptosis or rendering cells sensitive to apoptotic stimuli, for example in tumors that are not sensitive to such stimuli. Alternatively, in instances where one wishes to avoid apoptosis, for example in stroke or Alzheimer's disease, an agent that inhibits RKIP activity can be useful. In order to modulate apoptosis according to the invention, one administers an agent that modulates the activity of an RKIP motif-containing polypeptide to an individual in need of such treatment. Success may be monitored by, for example, monitoring the size of a tumor, or by monitoring the numbers of apoptotic cells in tissue biopsies. Alternatively, in the case in which one seeks to reduce apoptosis, success may be monitored by biopsies, or by monitoring the progression or regression of disease symptoms. For example, the percent occlusion of major vessels may be monitored to measure success in treatment or prevention of atherosclerosis. If the percent occlusion decreases as defined herein or does not increase, the treatment is successful. In treatment of Alzheimer's, standard indices of a patient's mental status may be used to monitor the success of treatment. An improvement in status during the course of treatment is indicative of successful treatment.

Methods for monitoring apoptosis are well known in the art, and include, for example, enzyme-based assays that detect chromosome fragmentation, electrophoretic assays that detect the same phenomenon (DNA "laddering"), FACS analyses that detect the degree of intercalation of a dye and morphological characterization of cells in tissue samples. A method of modulating apoptosis according to the invention is successful if it results in at least a 20% increase or decrease in apoptosis, depending on the desired effect, and preferably at least a 35%, 50%, 75%, 90%, 95% or even a 100% (or greater, in the case of induction of apoptosis) change in the level of apoptosis after treatment.

Dosage and Administration

The present invention provides for pharmaceutical compositions comprising a therapeutically effective amount of an agent that modulates the activity of an RKIP motif-containing polypeptide in combination with a pharmaceutically acceptable carrier or excipient. Such carriers include, but are not limited to, saline, buffered saline, dextrose, water, glycerol, ethanol, and combinations thereof. The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Alternative means for systemic administration include transmucosal and transdermal administration using penetrants such as bile salts or fusidic acids or other detergents. In addition, if an agent can be formulated in an enteric or an encapsulated formulation, oral administration may also be possible.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

EXAMPLES

Example 1

Identification of RKIP Interacting Proteins.

Purified recombinant RKIP protein was tested for binding to the components of the Raf/MEK/ERK cascade. Similar conditions can be used to screen and test any other target of an RKIP family protein. As mentioned above, these conditions may also be adapted for use as a screening method for identifying agents that modulate RKIP-target interactions. For co-precipitation experiments of endogenous proteins, $2 \times 10^7$ Rat-1 cells were lysed by sonication in PBS, and the immunoprecipitates were washed 4 times with PBS. Otherwise cells were lysed as described (Guan and Dixon, Anal. Biochemistry 192:262–267, 1991). Antibodies that were used in the experiments include crafVI, a peptide antibody against the 12 C-terminal amino acids of Raf-1 (Hafner et al. Mol. Cell. Biol. 14:6696–6703, 1994); a Raf monoclonal antibody to the regulatory domain (Transduction Laboratories); anti-MEK H8 (Santa Cruz); anti-RKIP was raised in rabbits immunized with purified GST-RKIP; anti-HA, 12CA5 monoclonal antibody; monoclonal anti-phospho ERK (Sigma) and polyclonal anti-phospho-MEK antibodies (New England Biolabs); anti-GST (Pharmacia).

RKIP associated with BXB, full-length Raf-1, MEK-1 and more weakly with ERK-2, but not with Ras. RKIP binding was independent of Raf-1 kinase activity, not affected by phosphatidylethanolamine, and direct, as evidenced by the interaction of purified proteins produced in E.coli as shown in FIG. 2(b).

Similar interactions were also demonstrated between endogenous mammalian proteins. RKIP antiserum co-immunoprecipitated Raf-1, MEK, and ERK from Rat-1 cells. This was not due to cross-reactivity, because the RKIP antiserum failed to immunoprecipitate purified Raf-1, MEK-1 or ERK-2 individually as shown in FIG. 2(c). These interactions were also observed in reciprocal immunoprecipitations with antisera to Raf-1, MEK or ERK. Confocal microscopy revealed an extensive co-localization between Raf-1 and RKIP both in quiescent and Ras transformed cells as demonstrated in FIG. 2(d) suggesting that a fraction of Raf-1 and its inhibitor RKIP remain associated even under conditions which promote Raf-1 activation.

Example 2

Inhibition of RKIP Activity Using Antibodies

In one embodiment, the RKIP protein inhibiting agent can be an antibody specifically recognizing an RKIP motif. For example, to examine the relevance of the interaction between RKIP and the kinases of the Raf/MEK/ERK module in mammalian cells, endogenous RKIP was inhibited by antibody microinjection. Since the AP-1 transcription factor is a major target of Raf signaling (Kortenjann et al. Mol. Cell. Biol. 14:4815–4824, 1994; Rapp et al., Oncogene 9:3493–3498, 1994; Kolch et al. Oncogene 8:361–370, 1993), the influence of RKIP on AP-1 activity was tested as shown in FIG. 3.

Microinjections of antibodies and reporter genes were performed as described previously (Lavinsky et al. Proc. Natl. Acad. Sci. USA 95:2920–2925, 1998; Rose et al. J. Cell. Biol. 119:1405–1411, 1992). Briefly, quiescent Rat-1 cells were microinjected with the reporter plasmids and antibodies and either left unstimulated or treated with 200 ng/ml TPA or 20 μg/ml forskolin. The RKIP antiserum was purified over a GST-RKIP affinity column. NIH3T3 cells were stained with an activation specific anti-phospho-ERK monoclonal antibody (Sigma). ERK phosphorylation was quantified by densitometry. For this purpose areas with microinjected cells were randomly photographed, and the staining intensity of whole individual cells was measured using the PcBAS software.

Figure 3D:
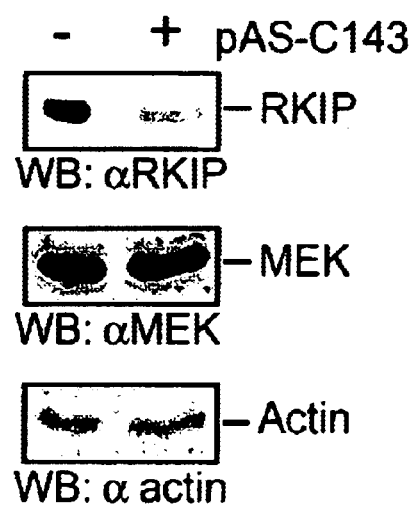
FIG. 3 shows that inhibition of endogenous RKIP activates AP-1 dependent transcription. a) Microinjection of anti-RKIP antibodies. Quiescent Rat-1 cells were microinjected with the indicated reporter plasmids and antibodies and either left unstimulated or treated with 200 ng/ml TPA or 20 $\mu$g/ml forskolin. b) The RKIP antisense vector, pAS-C143, downregulates expression of endogenous RKIP. NIH 3T3 cells were co-transfected with pAS-C143 and a GFP-expressing plasmid. GFP-positive cells were isolated by FACS and immunoblotted with indicated antibodies. c) The activity of an AP-1 reporter gene was measured in serum-starved or TPA-stimulated NIH 3T3 cells following co-transfection with RKIP antisense (pAS-C143) or empty vectors.
Figure 3E:
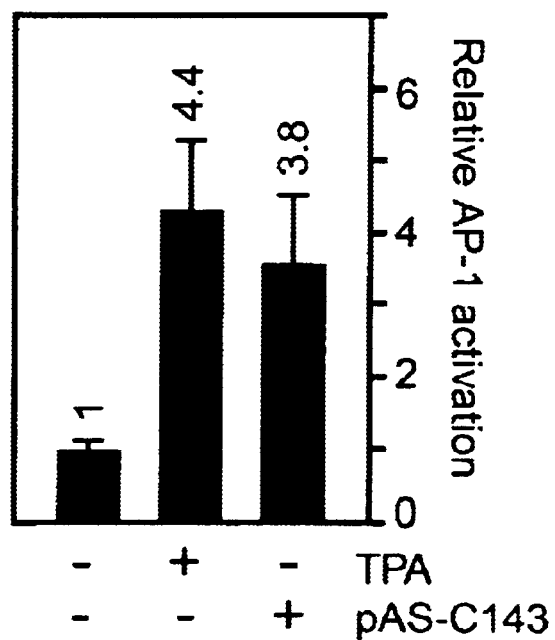

Microinjection of affinity purified anti-RKIP antibodies robustly activated a co-injected AP-1 dependent reporter gene in serum deprived Rat-i fibroblasts as shown in FIG. 3(a). This effect was highly specific, because (i) the injection of control IgG was ineffective; (ii) anti-RKIP IgG did not affect the expression of a cAMP dependent reporter gene; and (iii) co-injection of a RKIP expression vector abolished the AP-1 induction by anti-RKIP IgG. FIG. 2(a) shows that inhibition of endogenous RKIP using anti-RKIP antibodies activates AP-1 -dependent transcription.

Example 3

Inhibition of RKIP Activity Using Antisense Molecules

In one embodiment, the RKIP activity-modulating agent can be an antisense nucleic acid molecule specifically recognizing RKIP motif encoding nucleic acid. For example, we downregulated RKIP protein expression using the RKIP antisense vector, pASC143. The rat RKIP cDNA (Grandy et al. Mol. Endocrinol. 4:1370–1376, 1990) was cloned (i) into pcDNA3 to make p353/RKIP; (ii) into pCMV5 with a triple HA-tag at the N-terminus; and (iii) into pGEX-KG to make GST-RKIP. The pAS-C143 encompasses RKIP nucleotides 1–429 cloned into pCMVori in antisense orientation. pCMVori contains the CMV promoter, polylinker and polyadenylation sequences from pCMV5 inserted into pUCori upstream of the polyoma virus core origin (Gjorup et al. Proc. Natl. Acad. Sci. USA, 91:12125–12129, 1994) 6×His-tagged MEK- and GST-fusion proteins were expressed and purified as described (Hafner et al. Mol. Cell. Biol. 14:6696–6703, 1994) RKIP of>95% purity was prepared from GST-RKIP by thrombin cleavage (Guan and Dixon, Anal. Biochemistry 192:262–267, 1991) and subsequent FPLC separation over Superose (Kolch et al., Oncogene, 13:1305–1314, 1996).

The COS-1 cells were transfected as described (Catling et al., 1995, Mol. Cell. Biol. 15: 5214–5225) with 2 μg of HA-ERK-2, BXB, MEK and MEK-DD plasmids and the indicated amounts of p353/RKIP. The total amount of transfected DNA was kept constant using the appropriate vectors as carrier DNA. For RKIP downregulation experiments NIH 3T3 cells were transiently co-transfected using lipofectamine with 0.5 µg of pHACT 20 and 1.5 or 3 µg RKIP antisense expression vector (PAS-C143) or control vector (pCMVori) as indicated. pHACT expresses a truncated polyoma large T construct which has origin binding activity, but does not bind Rb or p53, and boosts the expression of pAS-C 143 to high levels. In addition, 0.1 µg of an AP1-Luc reporter was transfected for reporter gene assays. 48 hours post-transfection cells were serum starved for 20 hours and either left untreated or treated with TPA (200 ng/ml) or serum for 5 hours before being collected. Cells were lysed and cell extracts were used for immunoblotting or assayed for luciferase activity. For the GFP sorting experiments $5 \times 10^6$ NIH 3T3 cells were electroporated with either 100 µg pCMVori, 50 µg pCMV-GFP, and 50 µg pHACT or 100 µg pASC143, 50 µg CMV-GFP, and 50 µg CMV-HAC. Two days later cells were trypsinized and sorted for green fluorescent cells by preparative FACS. 100,000 GFP-positive cells were lysed in SDS-gel sample buffer and immunoblotted.

FIG. 3(b) shows that the RKIP antisense vector, pAS-C 143, downregulates expression of endogenous RKIP. NIH 3T3 cells were co-transfected with pAS-C 143 and a GFP-expressing plasmid. GFP-positive cells were isolated by FACS and immunoblotted with indicated antibodies. FIG. 3(c) shows the measurements of the activity of an AP-1 reporter gene in serum-starved or TPA-stimulated NIH 3T3 cells following co-transfection with RKIP anti sense (pAS-C 143) or empty vectors. This vector markedly reduced RKIP protein levels without affecting the expression of MEK-1 or actin as shown in FIG. 3(b). The pAS-C143 substantially induced the AP-1 reporter gene in serum-starved NIH 3T3 cells shown in FIG. 3(c). These data confirm the microinjection results and demonstrate that RKIP suppresses the Raf/MEK/ERK pathway.

Example 4

Inhibition of Raf Induced AP-1 Activation and Transformation by RKIP Motif

Figure 4A:
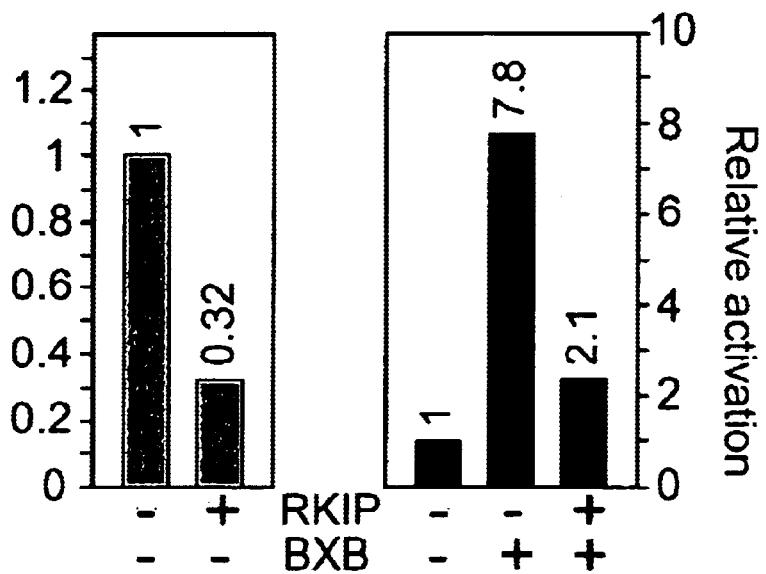
FIG. 4 shows that RKIP inhibits Raf- induced AP-1 activation and transformation. a) RKIP reduces basal and BXB-induced AP-1 activity in NIH 3T3 cells co-transfected with a 3×TRE-CAT reporter and the indicated expression plasmids. b) RKIP blocks BXB- but not ERK-induced AP-1 activation. Rat-1 cells were co-microinjected with a 4×TRE-lacZ reporter and the indicated expression vectors. c) RKIP inhibits Raf-dependent proliferation and transformation. NIH 3T3 cells were transfected with BXB, alone or together with RKIP (linked to neo). G4 18-resistant colonies were counted and scored for morphological transformation. Aliquots of the same transfection were allowed to grow to confluency without drug and were scored for focus formation. A BXB-transformed cell line was infected with LXSH-RKIP retrovirus or LXSH (hygromycin resistant) and seeded in soft agar in the presence of hygromycin. d) RKIP does not inhibit transformation by v-fos, v-src, or mutationally activated MEK in 208F or NIH cells. Data are expressed as reduction in focus formation relative to co-transfection with empty vector (set to 100%).
Figure 4B:
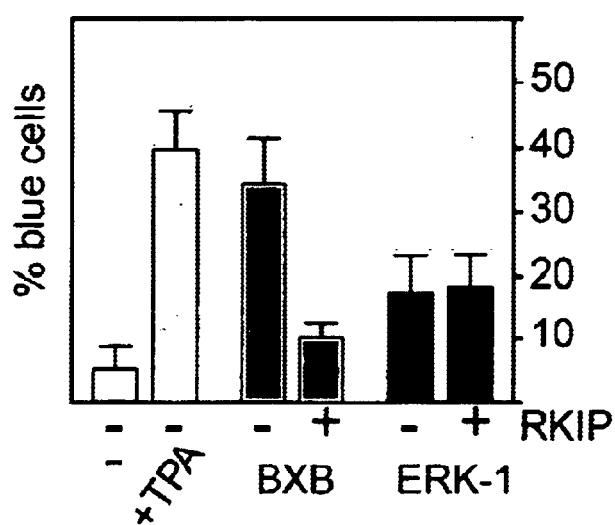
Figure 4C:
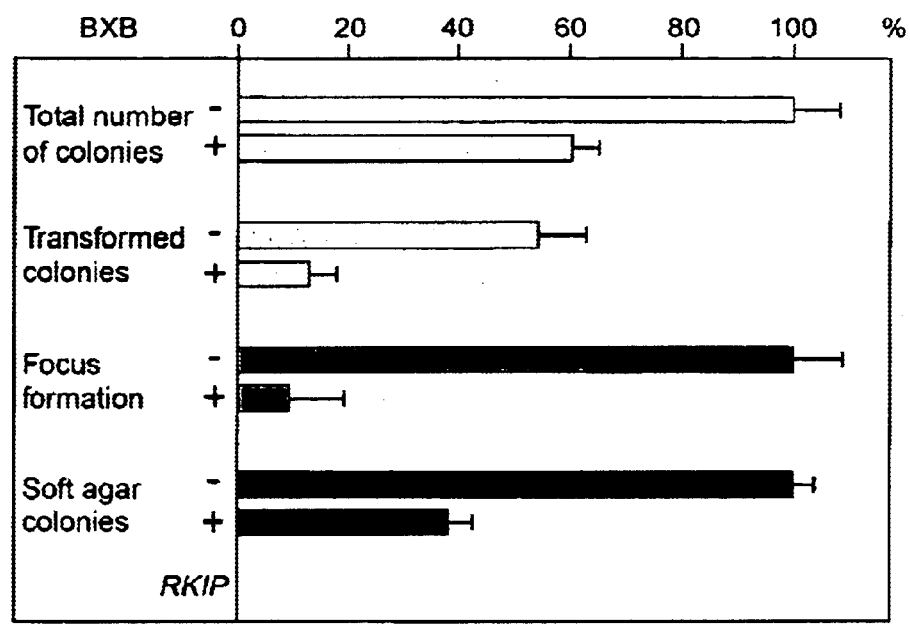

In one embodiment, the present invention provides a method of identifying a cell growth modulating agent by analyzing the effect of a candidate agent on the expression of an RKIP responsive reporter. For example, to show the effect of the RKIP on the activity of the AP-1 mediated transcription, NIH 3T3 cells were co-transfected with a 3×TRE-CAT reporter and the above described expression plasmids. NIH 3T3 and 208F cells were transfected in 6-well plates with 1 µg of pCMV5-BXB and 3 µg of p53/RKIP using Superfect (Qiagen). FIG. 4(a) shows that RKIP reduces basal and BXB-induced AP-1 activity in 3T3 cells. Further, Rat-1 cells were co-microinjected with a 4×TRE-lacZ reporter and the indicated expression vectors and FIG. 4(c) shows that RKIP blocks BXB- but not ERK-induced AP-1 activation.

Figure 4D:
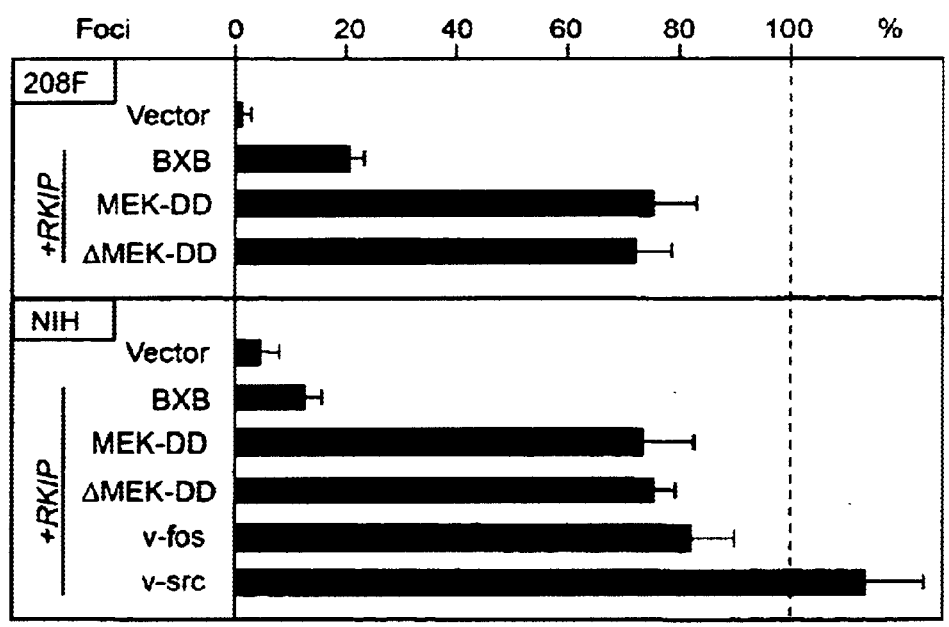

Additionally, NIH 3T3 cells were transfected with BXB, alone or together with RKIP (linked to neomycin/G418 resistance encoding gene). The G418-resistant colonies were counted and scored for morphological transformation. Aliquots of the same transfection were allowed to grow to confluency without drug and were scored for focus formation. A BXB-transformed cell line was infected with LXSH-RKIP retrovirus or LXSH (hygromycin resistant) and seeded in soft agar in the presence of hygromycin. FIG. 4(c) shows that RKIP inhibits Raf-dependent proliferation and transformation and FIG. 4(d) demonstrates that RKIP does not inhibit transformation by v-fos, v-src, or mutationally activated MEK in 208F or NIH cells. The data are expressed as the reduction in focus formation relative to focus formation upon co-transfection with empty vector (set to 100%).

Overexpression experiments further corroborated this conclusion. RKIP transfection diminished the basal as well as the BXB induced AP-1 activity as shown in FIG. 4(a), and microinjection of an RKIP expression vector impaired AP-1 induction by TPA and BXB as shown in FIG. 4(b). Notably, RKIP did not interfere with AP-1 stimulation by ERK-1.

Next, we tested the effects of RKIP overexpression in transformation assays. In contrast to transient reporter gene assays, transformation assays accommodate the complexity of cellular responses to the chronic deregulation of a single signaling component. RKIP significantly reduced the transformation efficiency of BXB in three distinct assays: morphological transformation, focus formation and anchorage independent growth shown, as in FIG. 4(c). RKIP also decreased total colony yield, albeit to a lesser extent than transformation demonstrating that RKIP interferes with Raf mediated proliferation as well as transformation. In contrast, RKIP impaired the induction of foci by v-fos or mutationally activated MEK alleles only to a small extent and failed to inhibit v-src transformation shown in FIG. 4(d). This indicates that RKIP specifically blocks transformation by the Raf/MEK/ERK pathway and accomplishes this primarily by inhibiting Raf. This is not to say, however, that RKIP or other RKIP family members act only upon this pathway. For example, there is evidence that RKIP inhibits kinases in the NF-κB pathway.

Example 5

Inhibition of Raf-1 Phosphorylation of MEK by RKIP

To dissect the effects of RKIP on individual activation steps, the Raf/MEK/ERK cascade was reconstructed in vitro using recombinant proteins and analyzing the phosphorylation of the protein components of said cascade.

Kinase assays were done as described in Hafner et al. (Mol. Cell. Biol. 14:6696–6703, 1994). Activated Raf-1 was generated by co-expressing GST-Raf-1 with v-Ras and Lck in Sf-9 cells and collected on glutathione Sepharose beads. Subsequent thrombin cleavage released Raf-1 which was fully active and >90% pure. To activate MEK and ERK in vitro, 20 ng activated Raf-1 was incubated with 40 ng purified His/MEK-1 and 250 ng GST-ERK-2 in Raf kinase buffer a containing 20 µM ATP for 20 minutes at 30° C. To measure kinase activities at individual steps the respective downstream components were omitted. The activation reactions were diluted into 50 µl Raf kinase buffer containing 20 µm ATP to yield equimolar concentrations of the kinases to be assayed and incubated with increasing amounts of purified RKIP on ice for 10 minutes. Similar assays may be performed with smaller polypeptides comprising RKIP motifs, or even with a peptide consisting essentially of an RKIP motif as defined herein. Then, 2 µCi [$^{32}$P]-γ-ATP and recombinant substrates were added and incubated for 20 minutes at 30° C. As substrates 200 ng kinase negative His/MEK-1 was used for Raf, 1 µg kinase negative GST-ERK for MEK, and 1 µg GST-ELK (New England Biolabs) for ERK. In some assays 1 µg GST-MEK was used as Raf-1 substrate with identical results.

FIG. 5(a) shows the effect of RKIP on the activation steps of the Raf/MEK/ERK cascade reconstituted in vitro with purified recombinant proteins. "BSA" indicates use of 15 µM bovine serum albumin; "Co." substrate alone; and "kn", kinase negative mutant. FIG. 5(b) shows that RKIP does not inhibit activated MEK. HA-MEK-DD or HA-MEK-1 expressed in COS-1 cells were immunoprecipitated with anti-HA antibodies from serum starved cells or TPA treated cells, respectively, and assayed for kinase activity. FIG. 5(c) shows that RKIP does not inhibit MEK phosphorylation by MEKK-1. MEKK-1 was immunoprecipitated from transiently transfected COS-1 cells and used to phosphorylate knMEK. Further, FIG. 5(d) indicates that RKIP does not inhibit Raf-1 autophosphorylation or phosphorylation of myelin basic protein (MBP).

RKIP decreased the phosphorylation of MEK by Raf-1, but did not inhibit ERK phosphorylation by MEK or ELK phosphorylation by ERK. In addition, RKIP (i) failed to inhibit MEK-DD, a constitutively active mutant of MEK, or MEK activated by TPA treatment of cells (FIG. 5(b)); (ii) did not prevent MEK phosphorylation by MEKK-1 (FIG. 5(c)); and (iii) did not interfere with Raf-1 autophosphorylation or phosphorylation of MBP by Raf-1 (FIG. 5(d)). These data indicate that RKIP is a very selective inhibitor that specifically blocks MEK activation by Raf. Again, this is not to say that Raf is the only target of RKIP or RKIP family members.

Example 6

In Vivo Regulation of MEK and ERK Activation by RKIP

Figure 6A:
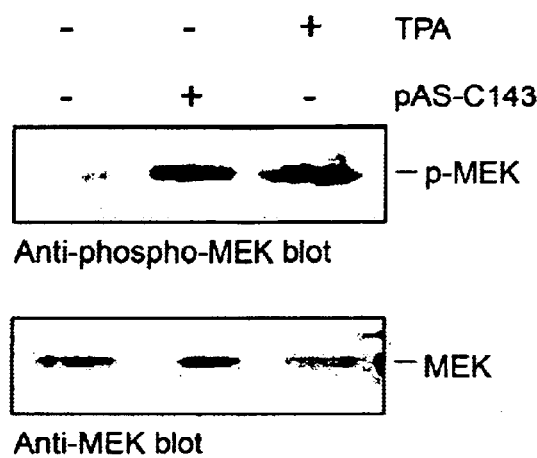
FIG. 6 shows that RKIP regulates MEK and ERK activation in vivo. a) RKIP downregulation activates MEK. NIH 3T3 cells were co-transfected with GFP and the RKIP antisense plasmid, pAS-C143. GFP positive cells were FACS sorted and immunoblotted with the indicated antisera. b) RKIP antibody microinjection enhances ERK activation. Quiescent NIH 3T3 cells were microinjected with anti-RKIP or control IgG and stimulated with 10 ng/ml TPA for 30 minutes. ERK activation was visualized with a monoclonal anti-phospho-ERK antibody (Sigma) and quantified densitometrically. c) RKIP inhibits MEK-1 activation. COS-1 cells were transiently transfected with HA-MEK and increasing amounts of RKIP expression vectors. Serum starved cells were stimulated with 100 ng/ml TPA for 20 minutes, and the kinase activities of RAF-1 and HA-MEK immunoprecipitates were measured. d) RKIP inhibits stimulation of ERK by v-Ras and v-Src. COS-1 cells were transfected with the indicated expression plasmids plus increasing amounts of RKIP HA-ERK-2 was immunoprecipitated and assay with MBP. e) RKIP inhibits ERK activation by BXB, but not by MEK-DD. COS-1 cells were transfected with the indicated expression vectors and the kinase activity of HA-ERK immunoprecipitates was examined.

FIG. 6(a) shows that RKIP downregulation activates MEK. NIH 3T3 cells were co-transfected with GFP and the RKIP antisense plasmid, pAS-C 143. GFP positive cells were FACS sorted and immunoblotted with the indicated antisera.

Figure 6B:
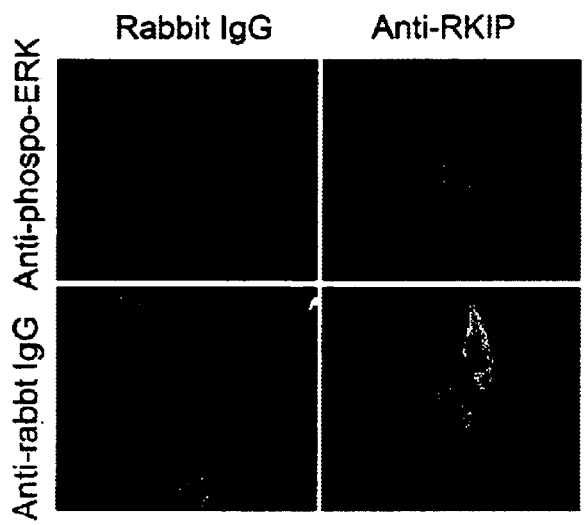

FIG. 6(b) demonstrates that RKIP antibody microinjection enhances ERK activation. Here, quiescent NIH 3T3 cells were microinjected with anti-RKIP or control IgG and stimulated with 10 ng/ml TPA for 30 minutes. ERK activation was visualized with a monoclonal anti-phospho-ERK antibody (Sigma) and quantified densitometrically.

Figure 6C:
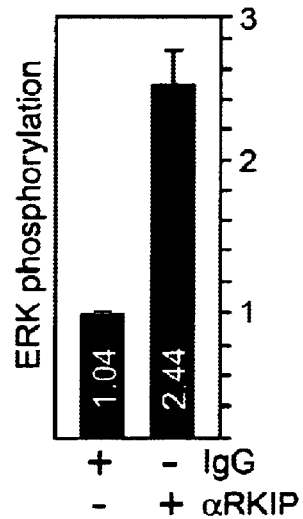

FIG. 6(c) shows that RKIP inhibits MEK-1 activation. COS-1 cells were transiently transfected with HA-MEK and increasing amounts of RKIP expression vectors. Serum starved cells were stimulated with 100 ng/ml TPA for 20 minutes, and the kinase activities of Raf-1 and HA-MEK immunoprecipitates were measured.

FIG. 6(d) shows that RKIP inhibits stimulation of ERK by v-Ras and v-Src. COS-1 cells were transfected with the indicated expression plasmids plus increasing amounts of RKIP. HA-ERK-2 was immunoprecipitated and assayed with MBP.

FIG. 6(e) shows that RKIP inhibits ERK activation by BXB, but not by MEK-DD. COS-1 cells were transfected with the indicated expression vectors and the kinase activity of HA-ERK immunoprecipitates was examined.

In vitro, RKIP disrupted the physical interaction between Raf-1 and MEK, which is required for MEK phosphorylation (Kolch et al., 1996, Oncogene 13: 1305–1314), and behaved like a competitive inhibitor for MEK. In vitro binding assays contained 5 μg of GST-fusion protein immobilized on glutathione Sepharose beads and 0.5–5μg purified recombinant protein in PBS supplemented with 10% bovine serum as nonspecific competitor. Sf-9 cell lysates were used as source of Raf proteins (Hafner et al., 1994, Mol. Cell. Biol. 14: 6696–6703). After incubation for 1 hour at 4° C. the samples were washed 4 times with PBS, resolved by SDS-PAGE and blotted. The blots were developed using ECL (Amersham).

Figure 7A:
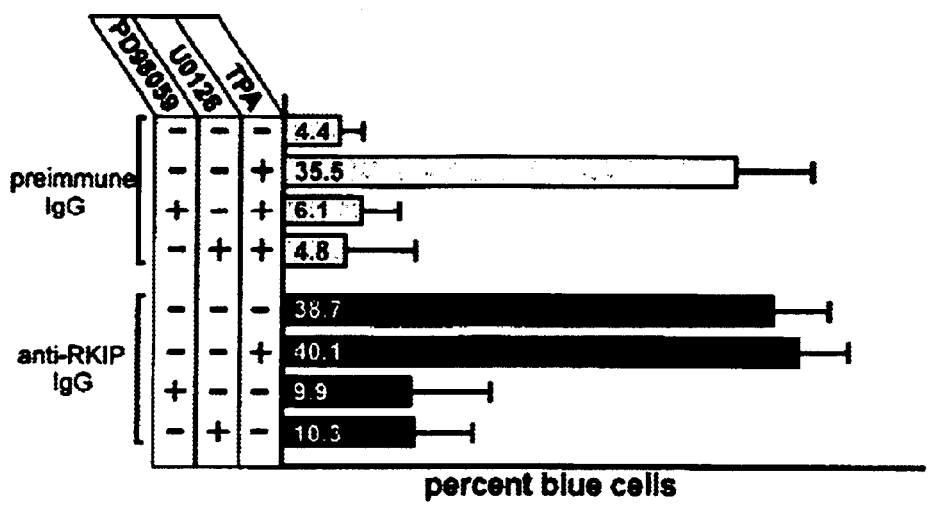
FIG. 7 shows that RKIP inhibits the ERK pathway by preventing MEK activation. (a) Rat-cells were microinjected with a TRE-LacZ reporter plasmid and affinity-purified RKIP antibodies or preimmune immunoglobulin G (IgG) and treated as indicated. The MEK Inhibitors PD98059 and U0125 were administered 1 h before microinjection of TPA (110 ng/ml). (b) RKIP antibodies prevent binding of RKIP to Raf-1 or MEK. GST, GST-RKIP, or GST-14-3-3 beads were incubated with saturating amounts of RKIP antibodies (I) or the corresponding preimmune serum (P) and tested for binding of Raf-1 or MEK 1. WB, Western blot. (c) The phosphorylation of kinase-negative MEK-1 (knMEK) by activated Raf-1 was examined in the presence (+) or absence (−) of 10 $\mu$M purified RKIP. RKIP was preincubated with RKIP antibodies or the corresponding preimmnune serum for 1 h.
Figure 7B:
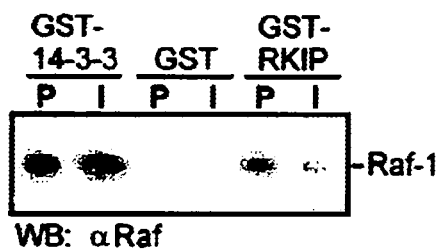
Figure 7C:
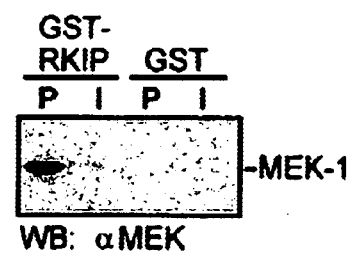
Figure 7D:
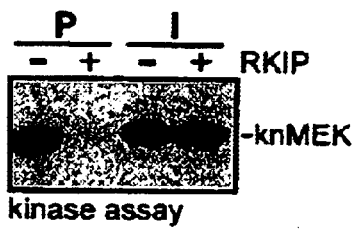

In addition, we investigated whether this mechanism also operated in cells. The downregulation of endogenous RKIP protein expression by the pAS-C 143 antisense vector substantially enhanced MEK phosphorylation on activation specific sites (FIG. 6a). Similarly, microinjection of RKIP antibodies enhanced ERK activation in NIH 3T3 cells (FIG. 6b). In a complementary approach RKIP was overexpressed. Co-transfection of RKIP had only a small influence on the activation of Raf-1 by TPA, but strongly inhibited the activation of MEK in a dose dependent fashion (FIG. 6c). The same results were observed in response to EGF (data not shown). RKIP overexpression also downregulated the activation of ERKs by v-Ras or v-Src oncogenes (FIG. 6d). Co-transfection of increasing amounts of a RKIP expression plasmid inhibited the BXB induced activation of ERK in a dose dependent manner. In contrast, RKIP did not affect ERK activation by MEK-DD (FIG. 6e). These data confirm the in vitro results (FIG. 5), and demonstrate that RKIP regulates the ERK pathway primarily at the Raf/MEK interface in vivo. Example 7. Activation of AP-1 dependent reporter gene by anti-RKIP antibodies AP-1 luciferase assays and microinjection experiments with affinity-purified RKIP antiserum and TRE-lacZ reporter plasmids were carried out as previously described (Yeung et al. Nature, 401:173–177, 1999). The microinjection of anti-RKIP antibodies raised against the full-length RKIP protein efficiently activated an AP-1 dependent reporter gene. This induction was due to the activation of MEK, since it could be suppressed by two structurally different MEK inhibitors, U0126 and PD98059 (FIG. 7(a)). This showed that the expression of the reporter gene is controlled by the ERK pathway and supports our previous conclusion that RKIP inhibits this pathway by downregulating the activation of MEK by Raf-1 (Yeung et al. Nature, 401:173–177, 1999). The induction of the reporter gene could be completely prevented by co-injection of an RKIP expression vector. (Yeung et al. Nature, 401:173–177, 1999), indicating that the RKIP antibodies specifically neutralized RKIP function. These antibodies are therefore useful tools for investigating the molecular mechanism by which RKIP works. The RKIP antiserum interfered with the binding of Raf-1 and MEK to RKIP (FIG. 7(b)). This effect was specific, as (i) the corresponding preimmune serum had no effect (ii) the RKIP antibodies did not prevent the binding of Raf-1 to 14-3-3. Furthermore, the RKIP antibodies reversed the inhibitory effect of RKIP on MEK phosphorylation by Raf-1 (FIG. 7(c)). These results indicated that the inhibitory effect of RKIP on MEK activation by Raf-1 depends on RKIP binding to Raf-1 and/or to MEK.

Figure 8A:
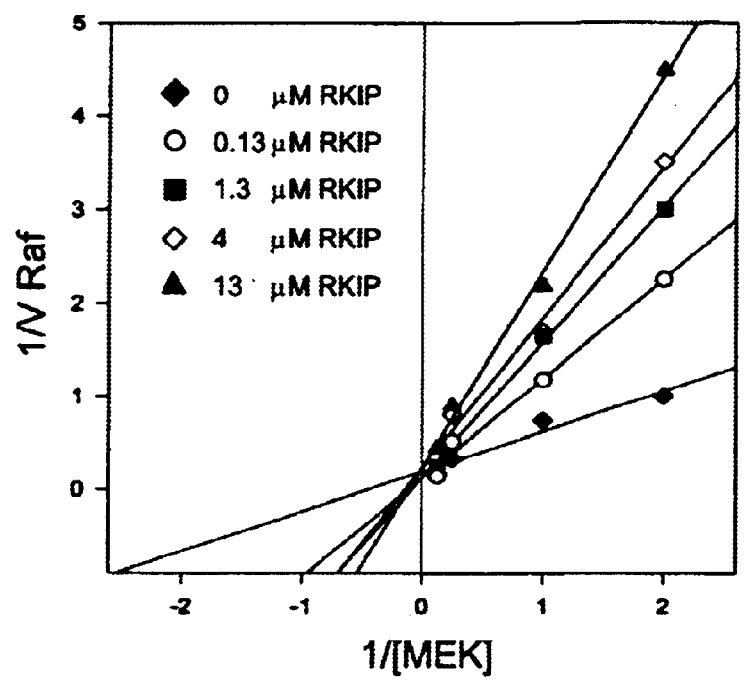
FIG. 8 shows that RKIP inhibits Raf-1 by a competitive mechanism. (a) Lineweaver-Burk plot of Raf-1 inhibition by RKIP. Activated GST-Raf-1 was used to phosphorylate GST-MEK-1 in the presence of increasing amounts of RKIP, as indicated. Phosphorylation was quantified with a Fuji phosphorimager. The data shown are the averages of three independent experiments. (b) RKIP disrupts the Raf-1 -MEK complexes. GST-MEK and Raf-1 were coexpressed in Sf-9 cells. The GST-MEK-Raf-1 complex was purified by adsorption to glutathione Sepharose beads, washed, and resuspended in PBS. Purified RKIP was added at the concentrations indicated. After 1 h at 4° C., the GST-MEK beads were washed three times with PBS and examined for associated proteins by Western blotting (WB) with the indicated antisera. (c) Raf-1 bound to RKIP does not phosphorylate MEK. A lysate of Sf-9 cells expressing activated Raf-1 was incubated with 5 $\mu$g of GST or GST-RKIP beads. Serial dilutions of the same lysate were immunoprecipitated with the anti-Raf serum crafVI. After three washes with PBS, the pellets were resuspended in kinase buffer and incubated with 100 $\mu$M ATP and kinase-negative MEK as substrate. MEK phosphorylation was visualized by immunoblotting with a phospho-MEK-specific antiserum. Raf-1 was stained with crafVI.

In addition, we studied the nature of RKIP binding. FIG. 8 shows that RKIP inhibits Raf-1 by a competitive mechanism. FIG. 8(a) shows a Lineweaver-Burk plot of Raf-1 inhibition by RKIP. Activated GST-Raf-1 was used to phosphorylate GST-MEK-1 in the presence of increasing amounts of RKIP, as indicated. Phosphorylation was quantified with a Fuji phosphorimager. The data shown are the averages of three independent experiments.

Figure 8B:
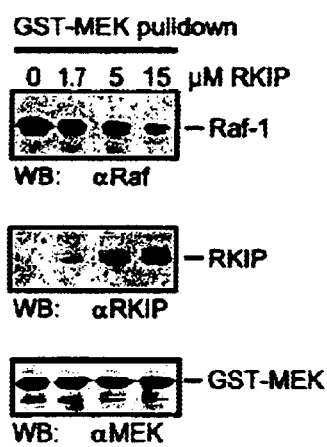

FIG. 8(b) shows that RKIP disrupts the Raf-1 -MEK complexes. GST-MEK and Raf-1 were co-expressed in Sf-9 cells. The GST-MEK-Raf-1 complex was purified by adsorption to glutathione Sepharose beads, washed, and resuspended in PBS. Purified RKIP was added at the concentrations indicated. After 1 hour at 4° C., the GST-MEK beads were washed three times with PBS and examined for associated proteins by Western blotting (WB) with the indicated antisera.

Figure 8C:
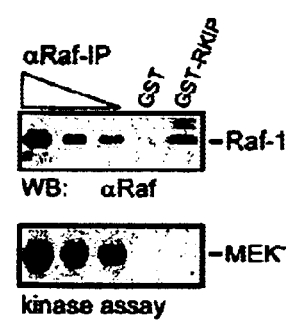

FIG. 8(c) demonstrates that Raf-1 bound to RKIP does not phosphorylate MEK. A lysate of Sf-9 cells expressing activated Raf-1 was incubated with 5 μg of GST or GST-RKIP beads. Serial dilutions of the same lysate were immunoprecipitated with the anti-Raf serum crafVI. After three washes with PBS, the pellets were resuspended in kinase buffer and incubated with 100 μM ATP and kinase-negative MEK as substrate. MEK phosphorylation was visualized by immunoblotting with a phospho-MEK-specific antiserum. Raf-1 was stained with crafVI.

Figure 9A:
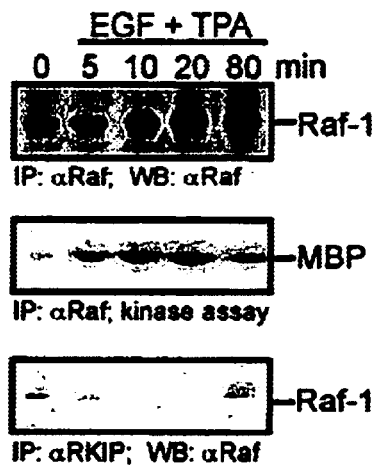
FIG. 9 shows an analysis of RKIP binding to activated Raf-1, MEK, and ERK. (a) Mitogen activation of Raf-1 decreases its association with RKIP. COS-1 cells were transiently transfected with Raf-1 and RKIP expression vectors. Serum-starved cells were treated with epidermal growth factor (EGF) (20 ng/ml) plus TPA (100 ng/ml) for the times indicated. Raf-1 immunoprecipitates were analyzed for kinase activity, and RKIP immunoprecipitates were examined for Raf-1, IP, Immunoprecipitation, WB, Western blot. (b) Purified RKIP produced in E. coli was tested for binding to GST-Raf and activated (?) GST-Raf beads. GST-Raf proteins were produced in Sf-9 cells and activated by coexpression of RasV12 and Lck. An aliquot of the GST-Raf beads was examined for phosphorylation of kinase-negative MEK (knMEK). (c and d) MEK and ERK proteins were phosphorylated in the presence of [$\gamma$-$^{32}$P]ATP and tested for binding to GST-RKIP beads. Binding of phosphorylated proteins was detected by autoradiography. Binding of total protein was visualized by Western blotting (WB). The contribution of phosphoproteins to the Western blot signal is minimal, because they represent less than 10% of the total protein.

These results also suggested that only the fraction of Raf-1 which is not bound to RKIP is available for activation. Therefore, we examined whether Raf-1 dissociates from RKIP during activation. For this purpose, RKIP and Raf-1 were co-expressed in COS-1 cells shown in FIG. 9(a). Raf-1 co-precipitated with RKIP in quiescent cells. Stimulation of the cells with tetradecanoyl phorbol acetate (TPA) plus epidermal growth factor caused an increase in Raf-1 kinase activity which correlated with a decrease of RKIP association. At later time points, as Raf-1 catalytic activity declined, the levels of Raf-1 co-precipitating with RKIP increased again.

Figure 9B:
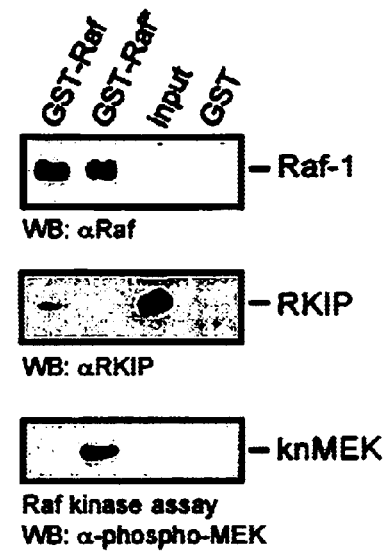
Figure 9C:
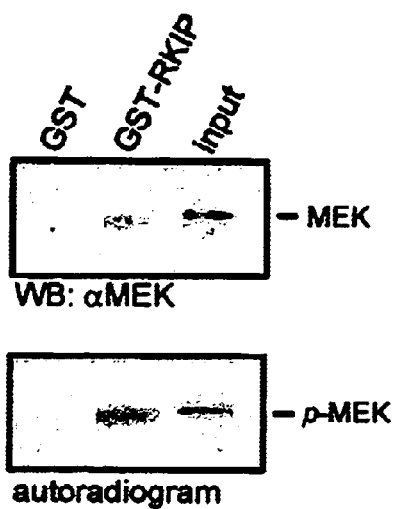
Figure 9D:
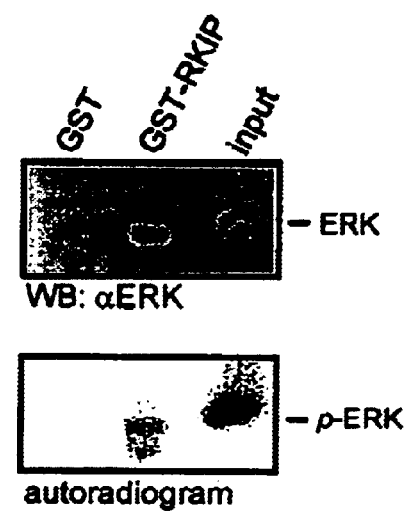

To investigate whether the changes in RKIP association are related to the activation status of Raf-1, the binding of purified RKIP to inactive and activated GST-Raf-1 beads was determined shown in FIG. 9(b). Activated GST-Raf-1 was produced in Sf-9 insect cells co-infected with RasV12 and Lck, which results in a robust activation of the catalytic activity. GST-Raf-1 proteins were purified by adsorption to glutathione Sepharose beads and incubated with recombinant RKIP produced in $E.\ coli$. Less RKIP bound to activated GST-Raf-1, indicating that Raf-1 activation weakens the affinity towards RKIP. This finding, however, did not seem to depend on the kinase activity of Raf-1 per se. Kinase-negative Raf-1 mutants, such as RafK375W (Kolch et al., 1991, Nature 349: 426–428) or RafS621A (Morrison et al., 1993, J. Biol. Chem. 268: 17309–17316), as well as activated Raf-1 mutants, such as RafS259D (Morrison et al., 1993, supra) or the isolated kinase domain BXB, bound to RKIP at levels comparable to that of the wild-type Raf-1 (Yeung et al., 1999, supra and data not shown). We also tested whether activation affected the binding of MEK and ERK to RKIP. Purified MEK and ERK were phosphorylated in vitro with recombinant Raf-1 or Raf-1 plus MEK, respectively, and incubated with GST or GST-RKIP beads. The binding reaction products were washed, separated on SDS gels, and immunoblotted with the appropriate antisera. We did not observe any differences in binding between activated and nonactivated forms. However, since only small fractions of MEK and ERK become phosphorylated, we also carried out the phosphorylation in the presence of [$\gamma$-$^{32}$P] ATP in order to avoid misinterpretation due to low phosphorylation efficiencies shown in FIGS. 9(c) and 9(d). The blots were autoradiographed to detect phosphorylated MEK and ERK and were subsequently stained with the cognate antisera to visualize total protein bound. Under these conditions, binding of phosphorylated MEK and ERK to RKIP was evident.

Example 8

Analysis of RKIP Interactions During the Cell Cycle.

Figure 10A:
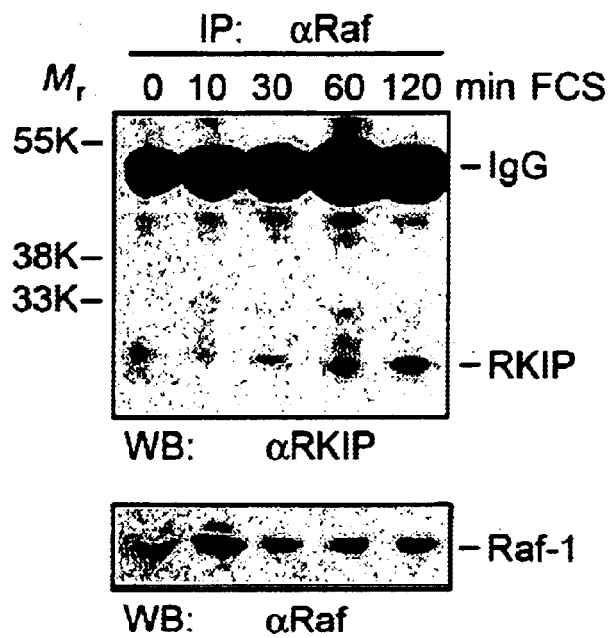
FIG. 10 shows that RKIP binding of Raf-1 decreases during mitogenic stimulation. Serum starved rat-1 cells were treated with 20% fetal calf serum for the indicated timepoints. a) Raf-1 immunoprecipitates were immunoblotted for associated RKIP. b) Cell lysates were examined for RKIP and ERK expression. ERK activation was monitored with a phospho-ERK specific antibody.
Figure 10B:
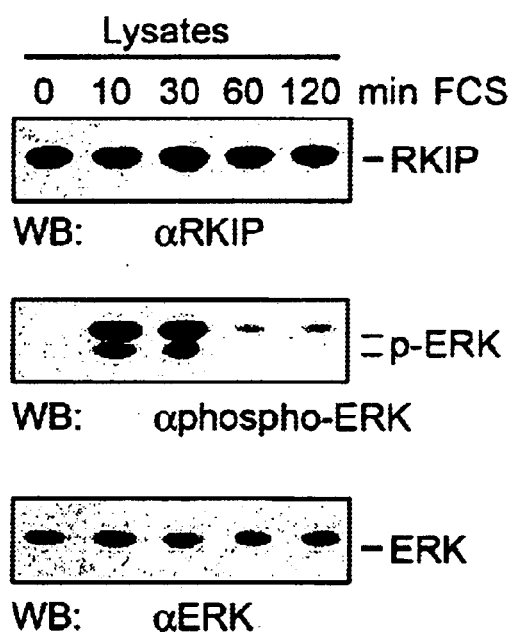

To examine whether the association between Raf and RKIP changes during mitogenic stimulation the presence of RKIP was monitored in Raf-1 immunoprecipitates prepared from Rat-1 cells at different timepoints after serum stimulation. FIG. 10 shows that RKIP binding to Raf-1 decreases during mitogenic stimulation. Serum starved Rat-1 cells were treated with 20% fetal calf serum for the indicated timepoints. FIG. 10(a) shows Raf-1 immunoprecipitates that were immunoblotted for associated RKIP. FIG. 10(b) shows cell lysates that were examined for RKIP and ERK expression. ERK activation was monitored with a phospho-ERK specific antibody.

The activation kinetics of the ERK pathway closely correlated with a decrease in RKIP co-precipitation. Furthermore, as the activity of the ERK pathway returned to basal levels at later times following mitogenic stimulation, the interaction between Raf-1 and RKIP returned to the level seen in quiescent cells.

Example 9

Constructs for the Analysis of RKIP Binding Motif According to the Present Invention Deletion mutants of pCMV-5-HA-RKIP (Yeung et al. Nature, 401:173–177, 1999) for expression in mammalian cells were generated by PCR. To construct FLAG-tagged Raf-1, the Raf-1 cDNA was PCR amplified for in-frame cloning into pCMV2-FLAG. For expression in $Escherichia\ coli$, deletion mutants were made as follows. GNX, which contains the BXB cDNA cloned into pGEX-KG (Haffier et el. Mol. Cell. Biol. 14:6696–6703, 1994), was cut with HindIII and other restriction enzymes as shown in FIG. 11. HindIII cuts downstream of the BXB cDNA and upstream of stop codons in all three reading frames. After blunt ending with T4 polymerase, the plasmids were re-ligated. The same strategy was used to make glutathione S-transferase (GST)-RKIP deletion mutants. MEK-1 deletion mutants were generated by PCR and cloned into pRSETA, resulting in the addition of an N-terminal six-His tag. Proteins were expressed and purified as described previously (Haffier et el. Mol. Cell. Biol. 14:6696–6703, 1994; Yeung et al. Nature, 401:173–177, 1999). Activated Raf-1 was purified from Sf-9 insect cells coinfected with GST-Raf-1 plus ResV12 and Lck as previously described (Mueller et al. EMBO J. 17:732–742, 1998) GST-MEK-1-Raf-1 complexes were produced in Sf-9 insect cells and purified by adsorption to glutathione Sepharose, as described previously (Mueller et al. EMBO J. 17:732–742, 1998).

Example 10

Analysis of RKIP Binding Motif According to the Present Invention

Typically, binding reactions between purified recombinant proteins were performed in phosphate-buffered saline (PBS) containing 10% bovine serum as a nonspecific competitor. Consistent results were obtained with 0.5 or 5% bovine serum albumin. After incubation for 1 to 5 hours at 4° C. with specific pull-down reagents, the samples were washed four times with PBS, resolved by sodium dodecyl sulfate (SDS)- polyacrylamide gel electrophoresis (PAGE) and blotted. Pulldown assays with the His/MEK-1 deletion mutants were performed by incubating 1 μg of soluble His/MEK-1 proteins with 1 μg of GST or GST fusion proteins immobilized on glutathione Sepharose beads in 0.75 ml of buffer containing 20 mM Tris-HCI (pH 7.4), 0.2 mM EDTA, 0.1 mM NaCl and 1 mM dithiothreitol. The beads were washed twice with the same buffer containing 0.1% NP40, resolved by SDS-PAGE, and immunoblotted with anti-His tag anti body (Qiagen).

Since full-length Raf-1 cannot be expressed in E. coli in an active form, Sf-9 insect cells infected with a Raf-1 baculovirus were used. Lysates were prepared by freeze thawing Sf-9 cells in PBS or by lysis in TBST (20 mM Tris HCl (pH 7.4), 150 mM NaCl, 2 mM EDTA, and 1% Triton X-100) supplemented with protease inhibitors (1 mM phenylmethysulfonyl fluoride and 1 µg of leupeptin/ml). Detergent-free lysis improved the recovery of complexes in the binding reactions but gave qualitatively the same results as Triton X-100 lysates. Lysates were clarified by centrifugation at 23,000 xg for 10 min. and the supernatants were used for the binding reactions. The blots were developed using chemiluminescence.

Figures 11A, 11B:
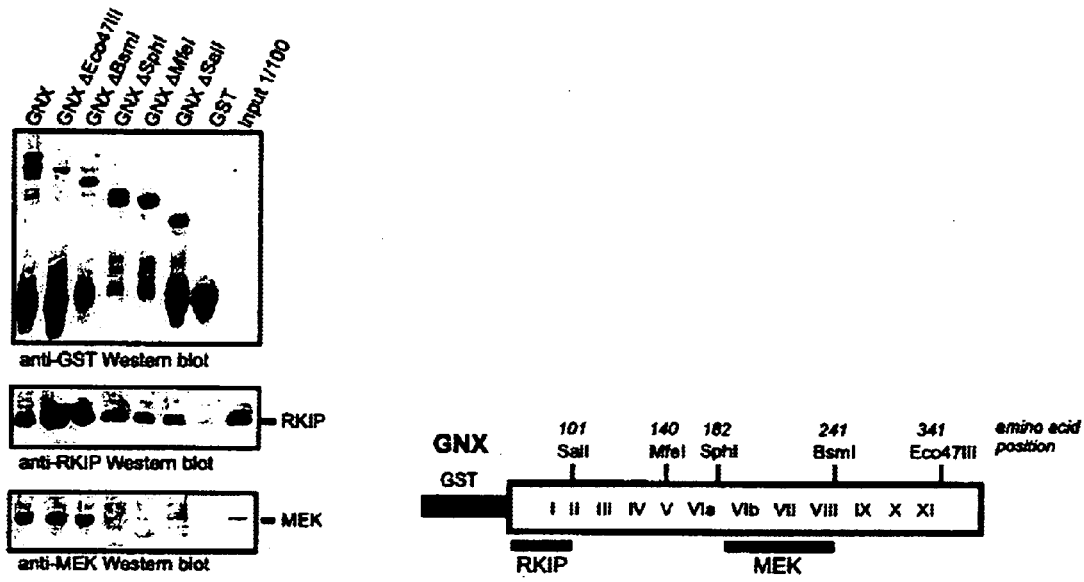
FIG. 11 shows an analysis of binding domains. (a) RKIP and MEK bind to different domains of the Raf-1 kinase. GST-tagged BXB, GNX, and the indicated deletion mutants were expressed in E. coli, immobilized on glutathione Sepharose beads, and incubated with purified RKIP or MEK-1. Proteins were visualized by Western blotting. The diagram illustrates the GNX regions deduced to be required for binding. Roman numerals refer to the kinase subdomains as defined by Hanks and Quinn. (b) RKIP and Raf-1 bind to different domains of MEK-1. Purified six-His-tagged MEK-1 deletion mutants were tested for binding to GST-RKIP beads (left panel) and GST-Raf-1 beads (right panel). His/MEK-1 proteins were detected by Western blotting with anti-His antibodies. The lower panel shows a schematic summary. nd, not done. (c) Analysis of Raf-1 and MEK binding sites in RKIP, GST-RKIP deletion mutants were tested for binding of MEK-1 and Raf-1. PEB, phosphatidylethanolamine binding motif.

FIG. 11(a) shows that RKIP and MEK bind to different domains of the Raf-1 kinase. GST-tagged BXB, GNX, and the indicated deletion mutants were expressed in E. coli, immobilized on glutathione Sepharose beads, and incubated with purified RKIP or MEK-1. Proteins were visualized by Western blotting. The diagram illustrates the GNX regions deduced to be required for binding. Roman numerals refer to the kinase subdomains as defined by Hanks and Quinn (Methods Enzymol. 200:38–62, 1991).

FIG. 11(b) shows that RKIP and Raf-1 bind to different domains of MEK-1. Purified six-His-tagged MEK-1 deletion mutants were tested for binding to GST-RKIP beads (left panel) and GST-Raf-1 beads (right panel). His/MEK-1 proteins were detected by Western blotting with anti-His antibodies. The lower panel shows a schematic summary. nd, not done.

Figures 11C, 11D:
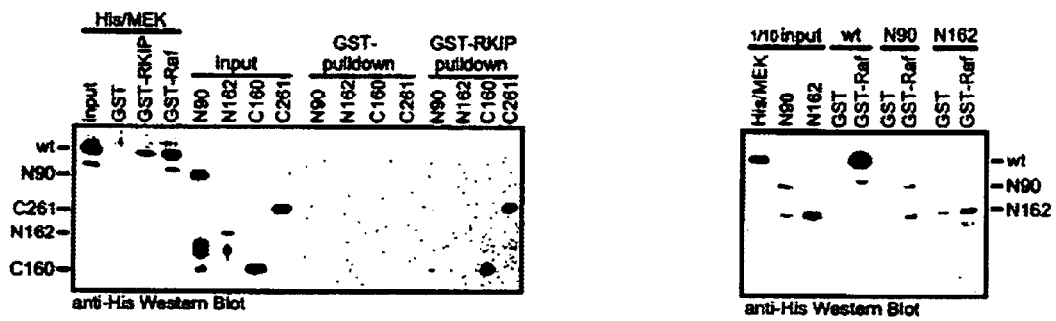

FIG. 11(c) shows the analysis of Raf-1 and MEK binding sites in RKIP, GST-RKIP deletion mutants were tested for binding of MEK-1 and Raf-1. PEB, phosphatidylethanolamine binding motif.

Phosphorylated His/MEK-1 for use in RKIP binding assays as shown in FIG. 11(c) was obtained by incubation with GST-Raf-1 immobilized on glutathione Sepharose in the presence of 20 µM ATP and 0.5 µCi of [γ$^{32}$P]ATP for 45 min. The GST-Raf-1 beads were removed by centrifugation. The supernatant was diluted fivefold with PBS and incubated with GST or GST-RKIP beads. To reduce nonspecific binding, the beads were preabsorbed with 10% serum or 2% bovine serum albumin for at lest 2 h. Typically, 0.5 to 2 µg of His-MEK-1 per binding reaction was used. Phosphorylated ERK was made in a similar fashion with the following modifications. The GST portion of GST ERK2 was removed by thrombin cleavage. GST-MEK was activated by GST-Raf-1 as described above except that only cold ATP was used. After 30 min., ERK2 and 0.5 [γ$^2$P]ATP were added and incubated for a further 15 min. The reaction was diluted five fold with PBS, and 20 µl of glutathione Sepharose beads was added to assure the removal of all GST-tagged proteins. The supernatant was used for the binding reactions. For some experiments, activated ERK purchased from New England Biolabs was used with consistent results.

These data were consistent with Raf-1 being the main regulatory target of RKIP. To further examine the molecular basis for the observed competitive mode of RKIP inhibition, we mapped the domains in the Raf-1 kinase domain, BXB, which are necessary for RKIP and MEK binding (FIG. 11a). BXB deletion mutants were expressed as GST fusion proteins in E. coli and were examined for binding to purified RKIP or MEK in vitro. Surprisingly, the required binding domains were different. Raf-1 kinase subdomains VIb to VIII were essential for MEK binding, whereas RKIP bound to subdomains I and II. The latter region contains the ATP binding site, but RKIP did not compete for ATP. Likewise, RKIP and Raf-1 bound to different domains in MEK-1 (FIG. 11b). Raf-1 bound to MEK-1 constructs containing the proline-rich region, whereas RKIP bound to the N-terminus of MEK-1. Thus, RKIP's ability to dissociate Raf-MEK complexes does not seem to involve a direct competition for the same binding sites. Rather, it must be due to an allosteric reduction of the binding affinity induced by RKIP or to mutual steric hindrance that excludes simultaneous binding of RKIP and Raf to MEK or of RKIP and MEK to Raf-1, respectively. When we mapped the binding sites of Raf-1 and MEK-1 to RKIP (FIG. 11c), the RKIP domain required for MEK binding could be clearly located, while Raf-1 interacted with multiple domains in RKIP. Notably, removal of the RKIP carboxy terminus up to the BspEI site enhanced Raf-1 association, whereas further deletion up to the PpuMI site decreased Raf-1 binding again. These data suggest that the interaction between Raf-1 and RKIP is complex, involving a main site of binding to amino acids 77 to 108 in the BspEI-PpuMI fragment, as well as minor contacts with several other domains. The partial overlap between the MEK and Raf-1 binding sites, however, is consistent with the observation that RKIP cannot bind Raf-1 and MEK simultaneously as shown in FIG. (12). FIG. 12(a) shows binding of recombinant purified RKIP with GST-MEK beads, Raf and MEK in the indicated combinations. FIG. 12(b) shows similar binding analysis using GST-RKIP beads; 12(c) with GST-ERK beads and 12(d) with GST-Raf beads. Binding assay was performed as described above.

Figure 13A:
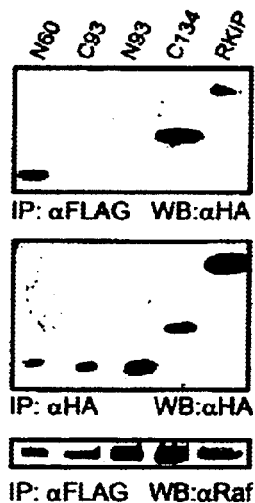
FIG. 13 shows that RKIP binding to Raf-1 or MEK is sufficient for inhibition. (a) Coimmunoprecipitation of RKIP deletion mutants with Raf-1. FLAG-Raf-1 and hemagglurinin (HA)-RKIP or HA-RKIP deletion mutants were coexpressed in COS cells. Lysates were immunoprecipitated (IP) with anti-FLAG antibodies, and associated HA-RKIP proteins were detected by Western blotting (WB) with anti-HA antibodies. PEB, phosphatidylethanolamine binding motif. (b) The effect of RKIP deletion mutants on Raf-induced AP-1 reporter gene expression. HA-RKIP mutants were cotransfected with the Raf-1 kinase domain, BXB, and an AP-1-luciferuse plasmid.
Figure 13B:
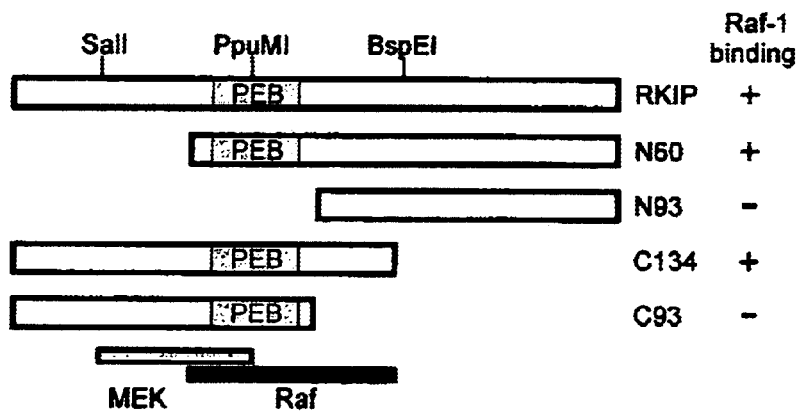
Figure 13C:
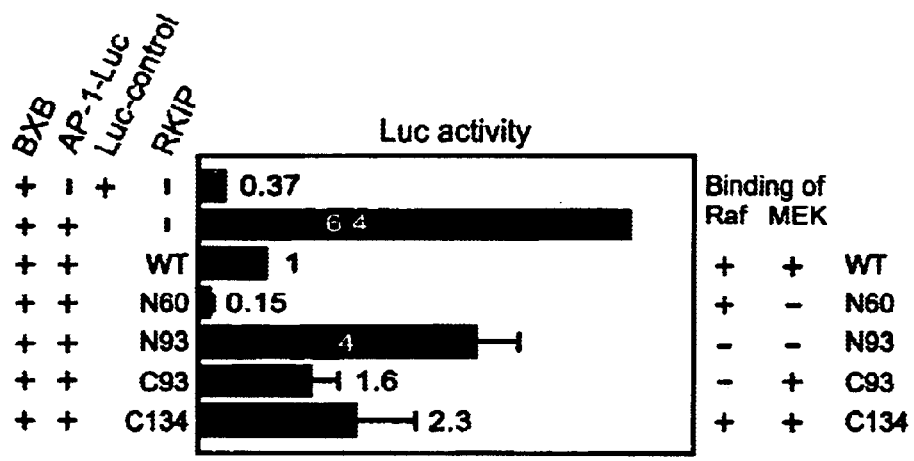

Finally, FIG. 13 shows that RKIP binding to Raf-1 or MEK is sufficient for inhibition. Deletion mutants suitable for expression in mammalian cells were generated. The analysis of Raf-1 binding to the RKIP deletion mutants was consistent with the in vitro mapping of the main Raf-1 binding site to amino acids 77 to 108 (FIG. 13a). The N93 and C93 RKIP mutants, which both disrupt this domain, failed to co-immunoprecipitate with Raf-1. However, C93 RKIP still contains the MEK binding domain. When tested for suppression of Raf-mediated AP-1 induction, only N93 RKIP showed a clear decrease in inhibitory activity (FIG. 13b). Since N93 RKIP is the only mutant that lacks both the Raf-1 and MEK interaction domains, we conclude that either Raf-1 or MEK-1 binding is sufficient for suppression of the ERK pathway.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of inhibiting the phosphorylation activity of a signal transduction kinase that binds an RKIP family member, wherein said signal transduction kinase is Raf-1 or MEK, comprising the step of contacting said signal transduction kinase with a polypeptide comprising an RKIP motif.

* * * * *

SEQUENCE LISTING

<160> NUMBER OF SEQ ID NOS: 11

<210> SEQ ID NO 1
<211> LENGTH: 94
<212> TYPE: PRT
<213> ORGANISM: Artificial Sequence
<220> FEATURE:
<223> OTHER INFORMATION: consensus sequence
<221> NAME/KEY: MISC_FEATURE
<222> LOCATION: (3)..(5)
<223> OTHER INFORMATION: Xaa = any amino acid
<221> NAME/KEY: MISC_FEATURE
<222> LOCATION: (9)..(9)
<223> OTHER INFORMATION: a hydrophobic amino acid residue
<221> NAME/KEY: MISC_FEATURE
<222> LOCATION: (11)..(13)
<223> OTHER INFORMATION: Xaa = any amino acid
<221> NAME/KEY: MISC_FEATURE
<222> LOCATION: (14)..(14)
<223> OTHER INFORMATION: a negatively charged amino acid residue
<221> NAME/KEY: MISC_FEATURE
<222> LOCATION: (15)..(18)
<223> OTHER INFORMATION: Xaa = any amino acid residue
<221> NAME/KEY: MISC_FEATURE
<222> LOCATION: (20)..(21)
<223> OTHER INFORMATION: Xaa = any amino acid residue
<221> NAME/KEY: MISC_FEATURE
<222> LOCATION: (23)..(72)
<223> OTHER INFORMATION: Xaa = any amino acid residue, 0 to 40 residues
      may be missing
<221> NAME/KEY: MISC_FEATURE
<222> LOCATION: (74)..(77)
<223> OTHER INFORMATION: Xaa = any amino acid residue
<221> NAME/KEY: MISC_FEATURE
<222> LOCATION: (79)..(82)
<223> OTHER INFORMATION: Xaa = any amino acid residue, 0 to 2 residues
      may be missing
<221> NAME/KEY: MISC_FEATURE
<222> LOCATION: (84)..(84)
<223> OTHER INFORMATION: Xaa = any amino acid residue
<221> NAME/KEY: MISC_FEATURE
<222> LOCATION: (87)..(87)
<223> OTHER INFORMATION: Xaa = an aromatic amino acid residue
<221> NAME/KEY: MISC_FEATURE
<222> LOCATION: (89)..(89)
<223> OTHER INFORMATION: Xaa = any amino acid residue
<221> NAME/KEY: MISC_FEATURE
<222> LOCATION: (90)..(90)
<223> OTHER INFORMATION: a hydrophobic amino acid residue
<221> NAME/KEY: MISC_FEATURE
<222> LOCATION: (91)..(93)
<223> OTHER INFORMATION: Xaa = any amino acid residue

<400> SEQUENCE: 1

Thr Leu Xaa Xaa Xaa Asp Pro Asp Glx Pro Xaa Xaa Xaa Asx Xaa Xaa
1               5                   10                  15

Xaa Xaa Glu Xaa Xaa His Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Tyr Xaa Xaa Xaa Xaa Pro Xaa Xaa
65                  70                  75                  80

Xaa Xaa Gly Xaa His Arg Xaa Val Xaa Glx Xaa Xaa Xaa Gln
                85                  90

<210> SEQ ID NO 2
<211> LENGTH: 187

```
<212> TYPE: PRT
<213> ORGANISM: Homo sapiens

<400> SEQUENCE: 2

Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Lys
    130                 135                 140

His Arg Gly Lys Phe Lys Val Ala Ser Phe Arg Lys Tyr Glu Leu
145                 150                 155                 160

Arg Ala Pro Val Ala Gly Thr Cys Tyr Gln Ala Glu Trp Lys Lys Tyr
                165                 170                 175

Val Pro Lys Leu Tyr Glu Gln Leu Ser Gly Lys
            180                 185

<210> SEQ ID NO 3
<211> LENGTH: 187
<212> TYPE: PRT
<213> ORGANISM: Mus musculus
<220> FEATURE:
<221> NAME/KEY: MISC_FEATURE
<222> LOCATION: (150)..(150)
<223> OTHER INFORMATION: Xaa = any amino acid residue

<400> SEQUENCE: 3

Met Ala Ala Asp Ile Ser Gln Trp Ala Gly Pro Leu Cys Leu Gln Glu
1               5                   10                  15

Val Asp Glu Pro Pro Gln His Ala Leu Arg Val Asp Tyr Ala Gly Val
            20                  25                  30

Thr Val Asp Glu Leu Gly Lys Val Leu Thr Pro Thr Gln Val Met Asn
        35                  40                  45

Arg Pro Ser Ser Ile Ser Trp Asp Gly Leu Asp Pro Gly Lys Leu Tyr
    50                  55                  60

Thr Leu Val Leu Thr Asp Pro Asp Ala Pro Ser Arg Lys Asp Pro Lys
65                  70                  75                  80

Phe Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Ser Gly Thr Ser Ile His Arg Tyr Val Trp Leu Val Tyr Glu Gln Glu
        115                 120                 125

Gln Pro Leu Ser Cys Asp Glu Pro Ile Leu Ser Asn Lys Ser Gly Asp
    130                 135                 140
```

```
Asn Arg Gly Lys Phe Xaa Val Glu Thr Phe Arg Lys Tyr Asn Leu
145                 150                 155                 160

Gly Ala Pro Val Ala Gly Thr Cys Tyr Gln Ala Glu Trp Asp Asp Tyr
            165                 170                 175

Val Pro Lys Leu Tyr Glu Gln Leu Ser Gly Lys
            180                 185

<210> SEQ ID NO 4
<211> LENGTH: 187
<212> TYPE: PRT
<213> ORGANISM: Drosophila

<400> SEQUENCE: 4

Met Ser Asp Ser Thr Val Cys Phe Ser Lys His Lys Ile Val Pro Asp
1               5                   10                  15

Ile Lys Thr Cys Pro Ala Thr Leu Leu Thr Val Thr Tyr Gly Gly
            20                  25                  30

Gly Gln Val Val Asp Val Gly Gly Glu Leu Thr Pro Thr Gln Val Gln
            35                  40                  45

Ser Gln Pro Lys Val Lys Trp Asp Ala Asp Pro Asn Ala Phe Tyr Thr
    50                  55                  60

Leu Leu Leu Thr Asp Pro Asp Ala Pro Ser Arg Lys Glu Pro Lys Phe
65                  70                  75                  80

Arg Glu Trp His His Trp Leu Val Val Asn Ile Pro Gly Asn Gln Val
                85                  90                  95

Glu Asn Gly Val Val Leu Thr Glu Tyr Val Gly Ala Gly Pro Pro Gln
            100                 105                 110

Gly Thr Gly Leu His Arg Tyr Val Phe Ile Val Phe Lys Gln Pro Gln
            115                 120                 125

Lys Leu Thr Cys Asn Glu Pro Lys Ile Pro Lys Thr Ser Gly Asp Lys
130                 135                 140

Arg Ala Asn Phe Ser Thr Ser Lys Phe Met Ser Lys Tyr Lys Leu Gly
145                 150                 155                 160

Asp Pro Ile Ala Gly Asn Phe Phe Gln Ala Gln Trp Asp Asp Tyr Val
            165                 170                 175

Pro Lys Leu Tyr Lys Gln Leu Ser Gly Lys Lys
            180                 185

<210> SEQ ID NO 5
<211> LENGTH: 220
<212> TYPE: PRT
<213> ORGANISM: C. elegans

<400> SEQUENCE: 5

Met Val Val Leu Val Thr Arg Ser Leu Leu Pro Ala Leu Phe Phe Ala
1               5                   10                  15

Ser Arg Ala Pro Phe Ala Ala Ala Thr Thr Ser Ala Arg Phe Gln Arg
            20                  25                  30

Gly Leu Ala Thr Met Ala Ala Glu Ala Phe Thr Lys His Glu Val Ile
            35                  40                  45

Pro Asp Val Leu Ala Ser Asn Pro Pro Ser Lys Val Val Ser Val Lys
    50                  55                  60

Phe Asn Ser Gly Val Glu Ala Asn Leu Gly Asn Val Leu Thr Pro Thr
65                  70                  75                  80

Gln Val Lys Asp Thr Pro Glu Val Lys Trp Asp Ala Glu Pro Gly Ala
                85                  90                  95
```

```
Leu Tyr Thr Leu Thr Lys Thr Asp Pro Asp Ala Pro Ser Arg Lys Glu
            100                 105                 110

Pro Thr Tyr Arg Glu Trp His His Trp Leu Val Val Asn Ile Pro Gly
        115                 120                 125

Asn Asp Ile Ala Lys Gly Asp Thr Leu Ser Glu Tyr Ile Gly Ala Gly
        130                 135                 140

Pro Pro Lys Thr Gly Leu His Arg Tyr Val Tyr Leu Ile Tyr Lys Gln
145                 150                 155                 160

Ser Gly Arg Ile Glu Asp Ala Glu His Gly Arg Leu Thr Asn Thr Ser
                165                 170                 175

Gly Asp Lys Arg Gly Gly Trp Lys Ala Ala Asp Phe Val Ala Lys His
                180                 185                 190

Lys Leu Gly Ala Pro Val Phe Gly Asn Leu Phe Gln Ala Glu Tyr Asp
            195                 200                 205

Asp Tyr Val Pro Ile Leu Asn Lys Gln Leu Gly Ala
        210                 215                 220

<210> SEQ ID NO 6
<211> LENGTH: 181
<212> TYPE: PRT
<213> ORGANISM: Antirrhinum-CEN

<400> SEQUENCE: 6

Met Ala Ala Lys Val Ser Ser Asp Pro Leu Val Ile Gly Arg Val Ile
1               5                   10                  15

Gly Asp Val Val Asp His Phe Thr Ser Thr Val Lys Met Ser Val Ile
                20                  25                  30

Tyr Asn Ser Asn Asn Ser Ile Lys His Val Tyr Asn Gly His Glu Leu
            35                  40                  45

Phe Pro Ser Ala Val Thr Ser Thr Pro Arg Val Glu Val His Gly Gly
        50                  55                  60

Asp Met Arg Ser Phe Phe Thr Leu Ile Met Thr Asp Pro Asp Val Pro
65                  70                  75                  80

Gly Pro Ser Asp Pro Tyr Leu Arg Glu His Leu His Trp Ile Val Thr
                85                  90                  95

Asp Ile Pro Gly Thr Thr Asp Ser Ser Phe Gly Lys Glu Val Val Ser
            100                 105                 110

Tyr Glu Met Pro Arg Pro Asn Ile Gly Ile His Arg Phe Val Phe Leu
        115                 120                 125

Leu Phe Lys Gln Lys Lys Arg Gly Gln Ala Met Leu Ser Pro Pro Val
    130                 135                 140

Val Cys Arg Asp Gly Phe Asn Thr Arg Lys Phe Thr Gln Glu Asn Glu
145                 150                 155                 160

Leu Gly Leu Pro Val Ala Ala Val Phe Phe Asn Cys Gln Arg Glu Thr
                165                 170                 175

Ala Ala Arg Arg Arg
            180

<210> SEQ ID NO 7
<211> LENGTH: 176
<212> TYPE: PRT
<213> ORGANISM: Aradopsis-TFL1

<400> SEQUENCE: 7

Met Glu Asn Met Gly Thr Arg Val Ile Glu Pro Leu Ile Met Gly Arg
1               5                   10                  15
```

-continued

```
Val Val Gly Asp Val Leu Asp Phe Phe Thr Pro Thr Thr Lys Met Asn
            20                  25                  30

Val Ser Tyr Asn Lys Lys Gln Val Asn Gly His Glu Leu Phe Pro Ser
        35                  40                  45

Ser Val Ser Ser Lys Pro Arg Val Glu Ile His Gly Gly Asp Leu Arg
    50                  55                  60

Ser Phe Phe Thr Leu Val Met Ile Asp Pro Asp Val Pro Gly Pro Ser
65                  70                  75                  80

Asp Pro Phe Leu Lys Glu His Leu His Trp Ile Val Thr Asn Ile Pro
                85                  90                  95

Gly Thr Thr Asp Ala Thr Phe Gly Lys Glu Val Val Ser Tyr Glu Leu
                100                 105                 110

Pro Arg Pro Ser Ile Gly Ile His Arg Phe Val Phe Val Leu Phe Arg
                115                 120                 125

Gln Lys Gln Arg Arg Val Ile Phe Pro Asn Ile Pro Ser Arg Asp His
            130                 135                 140

Phe Asn Thr Arg Lys Phe Ala Val Glu Tyr Asp Leu Gly Leu Pro Val
145                 150                 155                 160

Ala Ala Val Phe Phe Asn Ala Gln Arg Glu Thr Ala Ala Arg Lys Arg
                165                 170                 175
```

<210> SEQ ID NO 8
<211> LENGTH: 219
<212> TYPE: PRT
<213> ORGANISM: Yeast

<400> SEQUENCE: 8

```
Met Asn Gln Ala Ile Asp Phe Ala Gln Ala Ser Ile Asp Ser Tyr Lys
1               5                   10                  15

Lys His Gly Ile Leu Glu Asp Val Ile His Asp Thr Ser Phe Gln Pro
            20                  25                  30

Ser Gly Ile Leu Ala Val Glu Tyr Ser Ser Ser Ala Pro Val Ala Met
        35                  40                  45

Gly Asn Thr Leu Pro Thr Glu Lys Ala Arg Ser Lys Pro Gln Phe Gln
    50                  55                  60

Phe Thr Phe Asn Lys Gln Met Gln Lys Ser Val Pro Gln Ala Asn Ala
65                  70                  75                  80

Tyr Val Pro Gln Asp Asp Leu Phe Thr Leu Val Met Thr Asp Pro
                85                  90                  95

Asp Ala Pro Ser Lys Thr Asp His Lys Trp Ser Glu Phe Cys His Leu
                100                 105                 110

Val Glu Cys Asp Leu Lys Leu Leu Asn Glu Ala Thr His Glu Thr Ser
            115                 120                 125

Gly Ala Thr Glu Phe Phe Ala Ser Glu Phe Asn Thr Lys Gly Ser Asn
        130                 135                 140

Thr Leu Ile Glu Tyr Met Gly Pro Ala Pro Pro Lys Gly Ser Gly Pro
145                 150                 155                 160

His Arg Tyr Val Phe Leu Leu Tyr Lys Gln Pro Lys Gly Val Asp Ser
                165                 170                 175

Ser Lys Phe Ser Lys Ile Lys Asp Arg Pro Asn Trp Gly Tyr Gly Thr
            180                 185                 190

Pro Ala Thr Gly Val Gly Lys Trp Ala Lys Glu Asn Asn Leu Gln Leu
        195                 200                 205

Val Ala Ser Asn Phe Phe Tyr Ala Glu Thr Lys
```

```
<210> SEQ ID NO 9
<211> LENGTH: 189
<212> TYPE: DNA
<213> ORGANISM: Homo sapiens

<400> SEQUENCE: 9
accttggtcc tgacagaccc ggatgctccc agcaggaagg atcccaaata cagagaatgg        60
catcatttcc tggtggtcaa catgaagggc aatgacatca gcagtggcac agtcctctcc       120
gattatgtgg gctcggggcc tcccaagggc acaggcctgc accgctatgt ctggctggtt       180
tacgagcag                                                               189

<210> SEQ ID NO 10
<211> LENGTH: 7
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: n = C or G
<221> NAME/KEY: misc_feature
<223> OTHER INFORMATION: Consensus AP-1 binding site

<400> SEQUENCE: 10 tgantca                                                                   7

<210> SEQ ID NO 11
<211> LENGTH: 11
<212> TYPE: DNA
<213> ORGANISM: Artificial Sequence
<220> FEATURE:
<221> NAME/KEY: misc_feature
<223> OTHER INFORMATION: NF-kB binding element consensus sequence

<400> SEQUENCE: 11
ggggactttc c                                                             11
```